(12) United States Patent
McNair

(10) Patent No.: US 12,191,014 B1
(45) Date of Patent: Jan. 7, 2025

(54) PERSONAL ANALYSIS AND CHRONOTHERAPY

(71) Applicant: CERNER INNOVATION, INC., Kansas City, KS (US)

(72) Inventor: Douglas S. McNair, Leawood, KS (US)

(73) Assignee: CERNER INNOVATION, INC., Kansas City, MO (US)

( * ) Notice: Subject to any disclaimer, the term of this patent is extended or adjusted under 35 U.S.C. 154(b) by 5 days.

(21) Appl. No.: 15/855,137

(22) Filed: Dec. 27, 2017

Related U.S. Application Data

(62) Division of application No. 14/490,077, filed on Sep. 18, 2014, now Pat. No. 10,553,320.

(60) Provisional application No. 61/879,792, filed on Sep. 19, 2013.

(51) Int. Cl.
    *G16H 20/10* (2018.01)
    *G16H 10/00* (2018.01)
    *G16H 40/00* (2018.01)

(52) U.S. Cl.
    CPC .............. *G16H 20/10* (2018.01); *G16H 10/00* (2018.01); *G16H 40/00* (2018.01)

(58) Field of Classification Search
    CPC ......... G16H 20/10; G16H 10/00; G16H 40/00
    See application file for complete search history.

(56) References Cited

U.S. PATENT DOCUMENTS

| | | | |
|---|---|---|---|
| 6,322,503 B1 | 11/2001 | Sparhawk | |
| 6,801,859 B1 | 10/2004 | Friend et al. | |
| 8,533,075 B1 * | 9/2013 | Sayers, III | G16H 40/20 705/28 |
| 2006/0025672 A1 | 2/2006 | Sendai | |
| 2006/0149140 A1 | 7/2006 | Eldridge | |
| 2007/0276275 A1 | 11/2007 | Proctor et al. | |
| 2008/0140572 A1 | 6/2008 | Jackson | |
| 2011/0066055 A1 | 3/2011 | Bharmi et al. | |
| 2011/0119212 A1 * | 5/2011 | De Bruin | A61B 5/369 706/12 |
| 2011/0125238 A1 * | 5/2011 | Nofzinger | A61F 7/02 607/109 |

(Continued)

OTHER PUBLICATIONS

Final Office Action dated Jun. 29, 2018 in U.S. Appl. No. 14/490,077, 24 pages.

(Continued)

*Primary Examiner* — Chad A Newton

(74) *Attorney, Agent, or Firm* — Mughal Gaudry & Franklin PC

(57) ABSTRACT

A system, method and article of manufacture are presented for improving therapy such as adjustment of a chronotherapeutic pharmaceutical regimen. Physiological variables are measured longitudinally and a time series of the measurements is constructed. In some cases, a time series is pre-whitened and transformed to a frequency spectrum while applying multi-taper filtering, and entropy or other statistical measures are calculated for the power spectral distribution. Improved timing, medication and dosage are individually or collectively improved and/or verified through successive testing. An improvement is illustrated for hypertension, using medication to achieve autonomic control and to reduce blood pressure variability and to reduce spectral diversion.

18 Claims, 10 Drawing Sheets

(56) References Cited

U.S. PATENT DOCUMENTS

| | | | | |
|---|---|---|---|---|
| 2011/0306845 | A1* | 12/2011 | Osorio | G16H 50/20 600/300 |
| 2012/0156194 | A1* | 6/2012 | Arron | A61K 39/39566 424/131.1 |
| 2012/0323796 | A1* | 12/2012 | Udani | G16H 10/20 705/80 |
| 2013/0117696 | A1 | 5/2013 | Robertson et al. | |
| 2013/0172774 | A1* | 7/2013 | Crowder | G16H 20/10 600/300 |
| 2013/0317567 | A1* | 11/2013 | Vallapureddy | G16H 40/67 607/59 |
| 2015/0048102 | A1* | 2/2015 | Dickie | A61J 1/03 221/2 |

OTHER PUBLICATIONS

Hermida, et al., "Chronotherapy of hypertension: Administration-Time-Dependent Effects of Treatment on the Circadian Pattern of Blood Pressure", Advanced Dug Delivery Reviews, vol. 59, Jun. 28, 2007, pp. 923-939.

Non-Final Office Action received for U.S. Appl. No. 14/490,077, mailed on Feb. 8, 2019, 24 pages.

Preinterview First Office Action dated Aug. 15, 2017 in U.S. Appl. No. 14/490,077, 5 pages.

First Action Interview—Office Action dated Oct. 19, 2017 in U.S. Appl. No. 14/490,077, 4 pages.

Balanov et al., "Synchronization: From Simple to Complex", Springer Series in Synergetics, 2009, 429 pages.

Cornélissen et al., "Chronobiology of High Blood Pressure", Scr Med (Brno), vol. 80, No. 4, Oct. 2007, pp. 157-166.

Cornélissen et al., "Chronobiology Predicts Actual and Proxy Outcomes When Dipping Fails", Hypertension, vol. 49, No. 1, Jan. 2007, pp. 237-239.

Cornélissen et al., "Opportunity of Detecting Pre-Hypertension: Worldwide Data on Blood Pressure Overswinging", Biomedicine & Pharmacotherapy, vol. 59, Suppl. 1, Oct. 2005, pp. S152-S157.

Flack et al., "Benefits of Once-Daily Therapies in the Treatment of Hypertension", Vascular Health and Risk Management, vol. 7, Dec. 20, 2011, pp. 777-787.

Germano et al., "Detection of a Diurnal Rhythm in Arterial Blood Pressure in the Evaluation of 24-Hour Antihypertensive Therapy", Clinical Cardiology, vol. 7, 1984, pp. 525-535.

Halberg et al., "Ambulatory Blood Pressure Monitoring: The Need of 7-Day Record", Scr. Med. (Brno), vol. 78, No. 2, 2005, pp. 83-88.

Katinas et al., "Time Microscopy for All Kinds of Data Including Circadian Clock Biology", Biomedicine & Pharmacotherapy, vol. 59, Suppl. 1, Oct. 2005, pp. S20-S23.

Syrseloudis et al., "Ambulatory Blood Pressure Monitoring in Resistant Hypertension", International Journal of Hypertension, Article ID 285612, 2011, 4 pages.

Yoshimoto et al., "Frequency Components of Systolic Blood Pressure Variability Reflect Vasomotor and Cardiac Sympathetic Functions in Conscious Rats", The Journal of Physiological Sciences, vol. 61, 2011, pp. 373-383.

* cited by examiner

| Untreated | 03:00 dose | 21:00 dose | 09:00 dose |
|---|---|---|---|
| 0.60 | 0.26 | 0.31 | 0.51 |
| Entropy Reference | $P < 0.02$ | $P < 0.05$ | $P > 0.79$ |
| Spectrum Reference | Permutation $\chi^2$ $P < 0.03$ [Good 2005] | $P < 0.08$ | $P > 0.84$ |

*FIG. 8.*

|  | Untreated | 03:00 dose | 21:00 dose | 09:00 dose |
|---|---|---|---|---|
| mean(SBP) | 143.7 | 125.4 | 126.9 | 126.7 |
| max(SBP) | 174 | 155 | 154 | 170 |
| min(SBP) | 115 | 101 | 101 | 102 |
| range(SBP) | 59 | 54 | 53 | 68 |
| SD(SBP) | 14.0 | 11.0 | 10.5 | 11.8 |
| CV%(SBP) | 9.7% | 8.8% | 8.3% | 9.3% |

FIG. 9.

PERSONAL ANALYSIS AND CHRONOTHERAPY

CROSS-REFERENCE TO RELATED APPLICATIONS

This application is a divisional of U.S. application Ser. No. 14/490,077, filed Sep. 14, 2014, which claims the benefit of U.S. Provisional Application No. 61/879,792 titled "PERSONAL ANALYSIS AND CHRONOTHERAPY," filed Sep. 19, 2013, both of which are hereby expressly incorporated by reference in their entirety.

INTRODUCTION

Traditional medicine aims at diagnosing a medical condition of a patient and establishing a treatment regimen that has demonstrated effectiveness through statistical trials across a population of subjects having a medical condition. Ideally, a remedy is found that mitigates one or more adverse effects of a medical condition for 100% of the subjects who have the condition. Ideally, prior study identifies possible adverse side-effects, and patients undergoing treatment look for symptoms of these side-effects, and if present, the side-effects are mitigated through additional medication, or through the prescription of an alternative remedy. Ideally, 100% of patients respond to the medication in the same way at the same time, and so a "best time" to take the medication can be established through population studies. Thus each patient is advised, based on population studies, to take a certain level dose at a certain time, e.g. 100 mg at bedtime, 10 days after the beginning of the menstrual cycle, on an empty stomach, with a meal, etc.

Traditional medicine is particularly effective when extraordinary measures are required to preserve the life or health of a patient. An acute medical condition frequently calls for the constant monitoring and adjustment of a well-trained clinician to assure that patient life and health are preserved. But at such times, side-effects and relative effectiveness of alternative regimens are secondary matters compared to imminent harm. Tailoring a treatment regimen for best individual response at the time of a health crisis is frequently not considered.

Unfortunately, the traditional approach is fraught with difficulties, particularly when there does not appear to be an imminent threat of an acute health crisis. Below a certain threshold of perceived emergency, nothing is done. When the patient is not experiencing an acute health crisis it is difficult to justify or fund constant analysis and adjustment. Frequently a clinician is not even sought out to perform a patient evaluation. Frequently a patient who does seek help reports extraneous unrelated symptoms and/or does not report or exhibit the most important symptoms at the time of examination. The result is sometimes a partial diagnosis or a failure to make an important diagnosis. Even when a correct diagnosis is made, frequently medication is not taken, or lifestyle changes suggested by an attending clinician are ignored, or not diligently practiced, in part because a condition does not yet represent an imminent health crisis. Frequently some patients have a physiological context that is abnormal, such that the patient response is atypical.

In the past, individualization of medical treatment has been elusive. An individual patient experience that is atypical requires repetitious office visits, re-evaluation, involving unwanted delay, risk, and cost. Individual response is typically discarded when it appears to be atypical and it is considered to be an exception that represents at most anecdotal practical experience. Individualization has been too low priority to be practiced for acute conditions and too cumbersome and cost-prohibitive for preventative measures, and non-acute conditions.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

Systems, articles, methods, and computer-readable storage media are provided for facilitating a method of personal health evaluation. Physiological variable(s) data such as raw or processed blood pressure readings are monitored, e.g. by sensing a pressure level and/or recording the level sensed. Data is logged to a first data record for at least a first period of a periodic time frame. In an embodiment, a first set of circadian statistics is evaluated for a first time period during a first treatment regimen. Individual performance of the first treatment regimen is reported based on the first set of circadian statistics. In an embodiment, data is logged to a second data record for at least a second period of a periodic time frame. A second set of circadian statistics is evaluated for a second time period during a second treatment regimen. A measure of individual performance is provided that compares the second set of circadian statistics to the first set of circadian statistics allowing a user to be aware of a comparison of the second treatment regimen relative to the first treatment regimen. In an embodiment, a set of circadian statistics includes a circadian variability measure such as an estimate of entropy. In an embodiment a user input is received indicating a continuation of the first treatment regimen. In an embodiment, a user input is received indicating an initiation of the second treatment regimen. In an embodiment data is sent from a local computer for processing, evaluation, reporting, aggregation, publication or annotation.

In one aspect a computer implemented method evaluates personal health for a monitored patient within a patient population. Individual relative performance is reported by comparing a first set of circadian statistics of a first treatment regimen to a second set of circadian statistics of a second treatment regimen. A set of circadian statistics is evaluated from logged bio-marker related data values. In an embodiment an indication of a patient event related to a treatment regimen is received. In an embodiment an indication of the time of a patient event related to a treatment regimen is received.

In one aspect, an article of manufacture facilitates successfully following and logging at least a first treatment regimen. The article of manufacture includes a first dose of a first formulation remedy for a first patient condition, and a second dose of a second formulation remedy for the first patient condition. The second dose is separate from the first dose. The second dose formulation differs substantially from the first dose formulation. A first systematic marking associated with the first does formulation indicates to a logging user a first treatment regimen. A second systematic marking associated with the second dose formulation indicates to a logging user a second treatment regimen. An index marking facilitates contact with a reporting service that evaluates circadian statistics and provides individual performance of a patient for a treatment regimen based on logged data for at least one period of a periodic time frame.

BRIEF DESCRIPTION OF THE DRAWINGS

Embodiments are described in detail below with reference to the attached drawing figures, wherein:

FIG. 8 presents a comparison of statistics related to circadian variability of a patient under different treatment regimens;

FIG. 9 presents a comparison of circadian statistics of a patient under different treatment regimens.

DETAILED DESCRIPTION

Figure 1A:
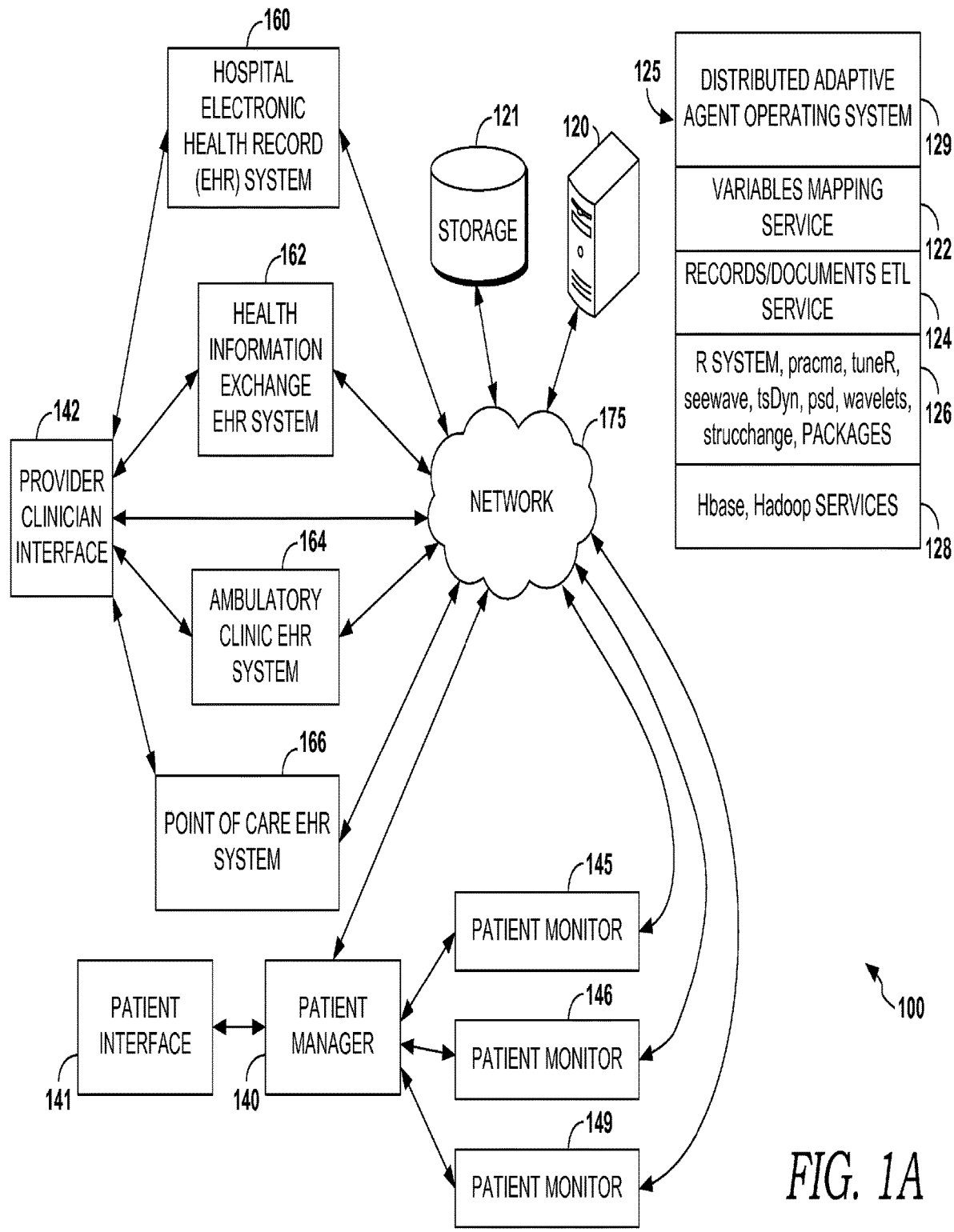
FIGS. 1A, 1B and 1C depict aspects of an exemplary operating environment suitable to implement embodiments of the present invention.

The subject matter of the present invention is described with specificity herein to meet statutory requirements. However, the description itself is not intended to limit the scope of this patent. Rather, the inventor has contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of our invention may be embodied as, among other things: a method, an article, a system, or a set of instructions embodied on one or more computer-readable media. Accordingly, the embodiments may take the form of a hardware embodiment, a software embodiment, or an embodiment combining software and hardware. In an embodiment, the invention takes the form of a computer-program product that includes computer-usable instructions embodied on one or more computer-readable media.

Computer-readable media include both volatile and nonvolatile media, removable nonremovable media, and contemplate media readable by a database, a switch, and various other network devices. By way of example, and not limitation, computer-readable media comprise media implemented in any method or technology for storing information, including computer-storage media and communications media. Examples of stored information include computer-useable instructions, data structures, program modules, and other data representations. Computer storage media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, other magnetic storage devices, and other storage devices. These technologies can store data momentarily, temporarily, or permanently.

Chronotherapy generally attempts to adjust a therapeutic regimen as a function of time by attempting to study one or more biological temporal rhythms, and to apply treatment relative to a chronobiological cycle. An embodiment of a therapeutic regimen is a baseline regimen consisting of no regimental activities, or a placebo regimen that provides inert or ineffective ingredients to be taken by a patient. A biological temporal rhythm is generally referred to as a chronobiological rhythm. A time frame that is divided into one or more time periods is generally referred to as a chronobiological cycle. For example, a consumption cycle might be defined as a period beginning with start of food consumption, followed by a period without food consumption. In another example, a daily digestion cycle might be defined as a cycle of three consecutive periods consisting of: a breakfast period, beginning with the start of breakfast and ending before the start of lunch; a lunch period, beginning with the start of lunch and ending before the start of supper; and a supper period, beginning with the start of supper and ending before breakfast. Likewise a weekly consumption cycle might be defined as a repeating sequence of seven daily digestion cycles with different meal times defined for each daily meal. Similarly, a daily digestion cycle might be defined as a breakfast cycle, a brunch snack cycle, a lunch cycle, an afternoon snack cycle, a supper cycle, and a bedtime snack cycle. Likewise, a menstrual cycle might be defined as a follicular phase, an ovulation phase and a luteal phase. Again, a menstrual cycle might be defined as a menstruation phase, a proliferation phase, and a secretory phase.

A circadian cycle generally refers to a chronobiological cycle of about a day. In an embodiment, a circadian cycle is defined as the waking time of a first day, to just before the waking time of a subsequent day. A circadian cycle might be defined as beginning at nightfall, and continuing to the nightfall of the consecutive day. A circadian cycle might be defined as a period of 24 hours beginning at a reference time such as midnight. A circadian cycle might be defined as a period of 24 hours beginning at a normal waking time for a subject such as 4:20 a.m.

Many pathophysiological circumstances vary during 24 h periods. Many physiologic processes undergo biological rhythms, including the sleep-wake rhythm and metabolism. Disruptive effects in the 24 h variations can manifest as the emergence or exacerbation of pathological conditions. So, chronotherapeutics is gaining increasing interest in experimental biology, medicine, pharmacy, and drug delivery.

An embodiment provides a system and method for informing a user of a comparative strength of alternative chronotherapeutic pharmaceutical regimens. A sequence of values is recorded measuring one or more physiological variables, constructing a time series from these measurements. In an embodiment the series is pre-whitened and transformed to provide a frequency spectrum, applying multiple-taper filtering. In an embodiment the entropy is calculated from a power spectral distribution, and statistical measures are used to compare the spectrum to reference spectra.

In an embodiment, two treatment regimens that differ in timing or dosage are compared and displayed to a user, allowing a user to determine comparatively better timing or dosage of pharmaceutical formulations so as to achieve a target level of circadian variability in terms of amplitude and phase spectra.

In an embodiment, a system and method are provided for optimizing chronotherapeutic pharmaceutical regimen, comprising longitudinally measuring one or more physiologic variables, constructing a time series from the measurements, pre-whitening the series, transforming the time series to a frequency spectrum, applying multiple-taper filtering, and calculating the entropy of the resulting power spectral distribution as well as statistical measures comparing said spectrum to reference spectra.

In an embodiment, individually tuned timing and dosage of pharmaceutical formulations are selected so as to achieve target levels of circadian variability in terms of amplitude and phase spectra. The application to the management of high blood pressure (hypertension) is illustrated. In this application, the technique facilitates normalization of autonomic control and blood pressure variability (BPV) and reduces spectral dispersion and polychromatic power spectral density, attenuating higher-frequency components. This is effective for mitigating health risks associated with excessive BPV.

Turning now to FIG. 1A there is presented an example operating environment 100 suitable for practicing embodiments of the invention. Example operating environment 100 includes a computerized system for compiling and/or running an embodiment of a chronotherapy architecture that supports a reporting service. With reference to FIG. 1A, one or more electronic health record (EHR) systems, such as hospital EHR system 160, health information exchange EHR system 162, ambulatory clinic EHR system 164, point of care EHR system 166 are communicatively coupled to network 175, which is communicatively coupled to computer system 120. In an embodiment, components of operating environment 100 that are shown as distinct components may be embodied as part of or within other components of environment 100. For example, the one or more EHR systems 160-166 may be implemented in computer system 120. Similarly, a single EHR system may perform functions for two or more of the example EHR systems shown in FIG. 1A.

In an embodiment, network 175 includes the Internet, and/or one or more public networks, private networks, other communications networks such as a cellular network, or similar network(s) for facilitating communication among devices connected through the network. In an embodiment network 175 is a local network or device interface such as a USB interface. Network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In an embodiment, operating environment 100 may include a firewall (not shown) between a first component and network 175. In such an embodiment, the firewall may reside on a second component located between the first component and network 175, such as on a server (not shown), or reside on another component within network 175, or may reside on or as part of the first component.

An embodiment of electronic health record (EHR) systems 160, 162, 164, and 166 include one or more data stores of health records, stored on storage 121. In an embodiment a data store includes one or more computers or servers that facilitate the storing and retrieval of the health records. In an embodiment, one or more EHR systems 160, 162, 164, and 166 are implemented as a cloud-based platform or may be distributed across multiple physical locations. In an embodiment EHR systems 160, 162, 164, and 166 further include record systems, which store real-time or near real-time patient (or user) information, such as information from wearable, bedside, or in-home patient monitors such as monitors 145, 146, or 149, for example.

Although FIG. 1A depicts multiple example EHR systems, it is contemplated that an embodiment employs only one EHR system, or alternatively, relies on user manager 140 and/or monitor 149 for storing and retrieving patient record information such as information acquired from monitor 149.

Example operating environment 100 further includes provider clinician interface 142 communicatively coupled to the one or more EHRs 160, 162, 164, and 166. A clinician is broadly, a health professional, or a worker who serves a patient in a clinical setting such as a doctor, consultant, health aid, nurse aid, nurse, nurse practitioner, specialist, etc. Although environment 100 depicts a direct communicative coupling between interface 142 and the one or more EHRs 160, 162, 164, and 166, it is contemplated that some embodiments of interface 142 may be communicatively coupled to the EHRs through network 175. Embodiments of interface 142 may take the form of a user interface operated by a software application or set of applications on a client computing device such as a personal computer, laptop, smartphone, or tablet computing device. In one embodiment, the application includes the PowerChart® software, manufactured by Cerner Corporation. In an embodiment, the application is a Web-based application or applet. Provider clinician application facilitates accessing and receiving information from a user or health care provider about a specific patient or set of patients for which chronotherapy analysis is to be performed and facilitates the display of results, recommendations or orders, for example. In some embodiments interface 142 also facilitates receiving orders for the patient from the clinician/user, based on the results. In some embodiments, interface 142 may also be used to display patient chronotherapy-information such as illustratively provided in FIGS. 4-9. Additionally, interface 142 is used to provide a report of individual performance, and to compare a first and second set of circadian statistics as discussed in connection to FIG. 2.

Example operating environment 100 further includes provider patient interface 141 communicatively coupled to storage 121, to computer 120 and to provider clinician interface 142. Although environment 100 depicts an indirect communicative coupling between interface 141 and the one or more patient monitors 145, 146, and 149, it is contemplated that an embodiment of interface 141 resides on patient monitor such as 149. An embodiment of interface 141 takes the form of a user interface operated by a software application or set of applications on a client computing device such as a personal computer, laptop, smartphone, or tablet computing device. In an embodiment the application is a client/server application, a client application, a server application, a browser plugin, or a mobile phone application. In an embodiment, the application is a Web-based application or applet. A patient application facilitates receiving information and indications from a user or health care provider about a specific patient or set of patients for which a circadian analysis is to be performed and facilitates the display of reports, comparisons, results, recommendations, or orders, for example. In an embodiment interface 141 also facilitates displaying a recommendation for a patient from a clinician, based on results. In an embodiment, interface 141 is used to display patient chronotherapy-information such as illustratively provided in FIGS. 4-9. Additionally, interface 141 is used to provide a report of individual performance, and to compare a first and second set of circadian statistics as discussed in connection to FIG. 2. Example operating environment 100 further includes computer system 120, which may take the form of a server, which is communicatively coupled through network 175 to patient monitors 145, 146, and 149, storage 121, and patient manager 140.

An embodiment of patient manager 140 takes the form of an application, which may be embodied as a software application operating on one or more mobile computing devices, tablets, smart-phones, front-end terminals in communication with back-end computing systems, laptops or other computing devices. In an embodiment, manager 140 includes a Web-based application or set of applications that is usable to manage user services provided by embodiments of the invention. For example, in an embodiment, manager 140 facilitates processing, logging, evaluating, interpreting, comparing, reporting, accessing, storing, retrieving, and communicating information acquired from monitor 149. In some embodiments, manager 140 is used to produce and/or report and/or compare and/or display user (or patient) chronotherapy information such as illustratively provided in FIGS. 4-9. Similarly, a user (who may be a patient) may access and view records of chronological patterns or analyses of previous time intervals using manager 140. Moreover, in some embodiments of manager 140, an interface component is used to facilitate access or input by a user of information or functions related to monitor 149, such as operational settings or parameters, a set of operational settings such as an evaluation template, an indication related to a patient event, a time of a patient event, a user identification, user data stored on monitor 149, and diagnostic services or firmware updates for monitor 149, for example.

As shown in example environment 100, manager 140 in an embodiment is communicatively coupled to monitor 149 and to network 175. In an embodiment of monitor 149 communicates via network 175 to computer 120 and/or storage 121 and/or clinician interface 142. An embodiment of monitor 149 comprises one or more sensor components, e.g. sensor 181 or 189 operable to acquire biometric or biological information about a user, such as information associated with a particular physical or mental state or the user, and which may be acquired periodically or as one or more time-series. In an embodiment monitor 149 is a web form that receives information from a user indicating data related to one or more physiological variables. In an embodiment, monitor 145 comprises a sensor or probe component operable for sensing a user's temporal activity, such as sensing EEG signals derived from the user.

Figure 1B:
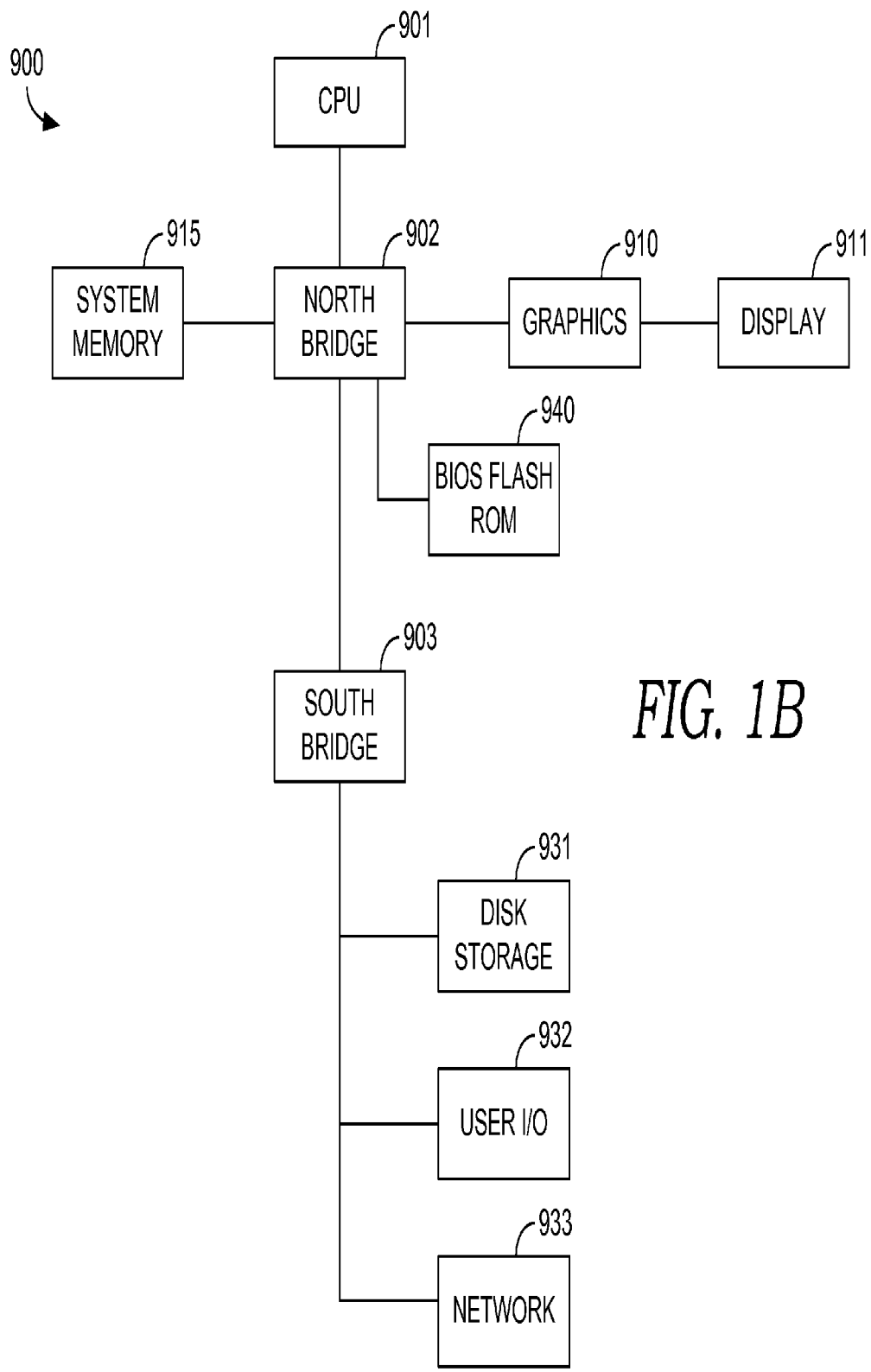
Figure 1C:
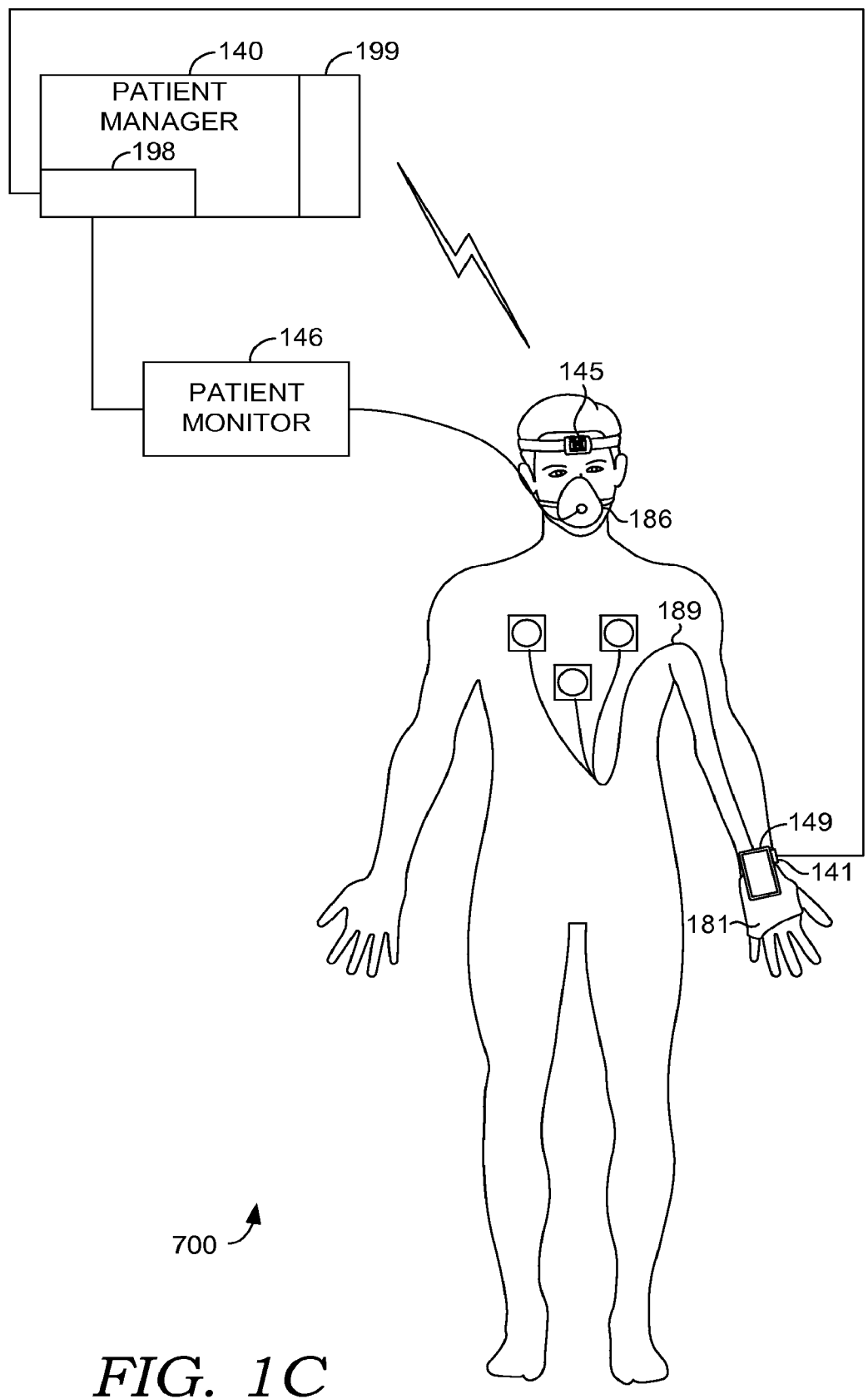

Turning briefly to FIG. 1C, patient physiological variables context diagram 700 illustrates a number of patient monitors (145, 146, and 149) for sensing various types of physiological measurements of variables. A monitor such as 145 may monitor muscle activity, which might be sensed from electromyogram signals, eye movement, which might be sensed from electro-oculogram signals, or other biometric information. In an embodiment a monitor such as 145 simply consists of a sensor probe, such as an EEG probe, and a communication link that periodically transmits identification information and probe data to interface 199 which in an embodiment is a network interface on a computer that performs the operations of patient manager 140, so that the time series of monitored values is stored on patient manager 140, enabling an associated computer to perform patient manager functions such as evaluating a circadian statistic, comparing circadian statistics, or reporting individual performance. In an embodiment patient monitor 146 collects raw sensor information such as optical sensor, and performs signal processing such as movement detection, kinematic modeling, distance and shape processing, velocity measurement, providing physiological-variable related data, trending, wavelet processing, thresholding, computational processing of time series, logical processing of data collected, etc. In an embodiment, a monitor such as patient monitor 149 communicates through interface 141 with a patient manager 140 through wired or wireless network interface 198, thus allowing patient manager 140 to perform multi-sensor or single sensor processing. In an embodiment interface 141 is one of an audio/microphone jack, a USB connector, a mini-USB connector, or a micro-USB connector. In an embodiment a monitor such as 146 makes use of a fingertip oximetry probe, to collect data that alarms on condition of hypotaxia/desaturation. In an embodiment, monitor 149 makes use of a first physiological-variable probe such as non-invasive blood pressure monitor (NIBP) 181 and a second physiological-variable probe such as cardiac probe cluster 189. Probe 181 is useful for irregularities in blood pressure such as unusually high or low mean arterial pressure, diastolic pressure or systolic pressure. Though monitor 149 is shown with two probe types, an embodiment of monitor 149 has an arbitrarily large number of probes for the same physiological variable or for many variables. In an embodiment, monitor 149 makes use of multi-sensor electrocardiogram probe 189. Probe 189 is useful for simultaneously measuring electrical activity of the heart, and respiration rate for detection of bradycardia, tachycardia, ventricular fibrillation, etc. In an embodiment probe 189 is used to detect respiration rate redundantly over three pairs of electrodes, allowing monitor 149 to collect data for detection of hyperventilation, hypoventilation, etc. An embodiment of a probe such as probe 189 monitors one or more of Pulmonary Capillary Web Pressure (PCWP), Left Atrium Pressure (LAP), Central Venous Pressure (CVP), Intra Cranial Pressure (ICP), Central Venous Oxygen Saturation (SCVO2), Hemoglobin Oxygen Saturation (SO2), Arterial Oxygen Saturation (SpO2), temperature, blood pressure, rate, temperature, or other physiological variable. An embodiment of monitor 146 tracks contractions and in-utero baby heart rate for a female subject during labor using a cardiotocometer probe. An embodiment of probe 189 monitors two patients who are linked, e.g. during gestation. An embodiment of monitor 146 tracks respiration directly through respiration probe 186. An embodiment of monitor 145 tracks temperature with a surface temperature probe. An embodiment of monitor 149 accumulates data over an observation period, and buffered data is transferred to patient manager 140 for non-real-time evaluation. An embodiment of monitor 145 includes a motion sensor, with accelerometer for sensing seizure, coughing, or motion. An embodiment of sensor 146 monitors breathing for logging of respiration during use of a constant positive airway pressure (CPAP) machine. An embodiment of monitor 146 measures time of use of an asthma inhaler. An embodiment of monitor 149 dispenses nitroglycerine and records time of use. An embodiment of monitor 149 is a metered pill container that records time of use of a pill. An embodiment of monitor 149 records time of incontinence by using a conductance probe. An embodiment of monitor 149 records user-provided reports of salient patient events.

In an embodiment, one or more sensor components of monitor 149 may comprise a user-wearable sensor component or sensor component integrated into the user's or patient's living environment. Examples of sensor components of monitor 149 include wherein the sensor is positioned on or near the user's head, attached to the user's clothing, worn around the user's head, neck, leg, arm, wrist, ankle, etc., skin-patch sensor, ingestible or sub-dermal sensor, or wherein sensor component(s) are integrated into the user's living environment (including the bed, pillow, or bathroom), sensors operable with or through a smart phone carried by the user, for example.

An embodiment of monitor 149 stores user-derived data locally, and/or communicates data over network 175 to be stored remotely. In an embodiment, manager 140 is wirelessly communicatively coupled to monitor 145. Manager 140 may also be embodied as a software application or app operating on a user's mobile device. In some embodiments, manager 140 and monitor 149 are functional components of the same device, such as a device comprising a sensor and a user interface. In some embodiments, manager 140 is embodied as a base station, which may also include functionality for charging monitor 149 or downloading information from monitor 149.

Additionally, an example embodiment of monitor 145 is shown in FIG. 1C. In this embodiment, monitor 145 is worn on the user's head and may be worn while the user is sleeping. Further, in an example embodiment, monitor 145 is attached to a strap to be worn around the user's head thereby positioning monitor 145 to be near the user's head. Additionally, the example embodiment of monitor 145 shown in FIG. 1C includes some functionality of manager 140. For example, this embodiment of monitor 145 includes a user interface with functionality for configuring operational settings, such as on and off or settings for storing and/or communicating sleep-related information acquired from the user information, such as uploading the information to manager 140 or to storage 121, and display functionality for viewing or reviewing sleep-related information acquired from the user. In one embodiment, monitor 145 is embodied as a Zeo™ sleep sensor headband manufactured by Zeo Inc. of Newton, Massachusetts.

Additionally, an example embodiment of monitor 149 is shown in FIG. 1C. In this embodiment, monitor 149 is worn on the user's hand, and wrist while the user is performing daily tasks. Further, in an exemplary embodiment, monitor 149 includes a probe 189 for sensing a cardiac signal. Additionally, the example embodiment of monitor 149 shown in FIG. 1C includes some functionality of manager 140. For example, this embodiment of monitor 149 includes a user interface with functionality for configuring operational settings, such as on and off or settings for storing and/or communicating chronotherapy information acquired from the user, and uploading the information to manager 140 or to storage 121, and display functionality for viewing or reviewing chronotherapy information acquired from the user. In an embodiment, monitor 149 is embodied as a Sotera™ sensor such as that manufactured by Sotera Wireless, Inc. of San Diego, California.

With reference to FIG. 1A, an embodiment of monitor 145 include analog-to-digital (A/D) converters for converting analog acquired information into digital information. For example, in one embodiment, user information is acquired at 512 samples per second. Because sleeping-related signals include low frequencies in comparison to other biological signals, an appropriate sampling rate is determined to adequately capture information sufficient to characterize a user's physiological information. For example, Delta or Theta cycles have comparatively low frequencies.

In an embodiment, monitor 149 includes functionality for processing user-derived information locally or for communicating the information to computer system 120 or manager 140, where it may be processed. In an embodiment, the processing may be carried out or facilitated by one or more software agents, as described below. In an embodiment the processing functionality, which may occur on monitor 149, manager 140 and/or computer system 120 includes signal conditioning, such as removing noise or erroneous information. In an embodiment processing functionality is operable to process user-derived information, such as NIBP data, as it is acquired, continuously or periodically such as every 10, 15, or 30, 60 seconds, every few minutes or at the end of a day. In an embodiment, the data is reduced into a time series with resolution of 5, 10, 15, 30, 60 seconds, or every few minutes. In an embodiment, the data from a day is decimated or resampled into a number of nearly orthogonal daily time series. For example, with data reduction to a single SBP/DBP pair every 15 seconds, 240 virtual days equivalent of data can be obtained by producing an hourly time series for each 15 second interval over a 24 hour period. In an embodiment, holes in data collection are interpolated through approximately linear randomized interpolation of data points. In an embodiment, the processing includes classifying the user-derived information acquired for a particular time interval into a circadian pattern category. For example, in some embodiments, monitor 149 samples a user's NIBP information and processes (or communicates to manager 149 or computer system 120 for processing) the information approximately every day to classify the user's stability pattern for that time interval. For example, every day, a user's blood pressure pattern may be determined to be one of normal dipper, circadian hyper-amplitude-tension (CHAT), non-dipper, extreme dipper, reverse dipper, and riser, etc. Likewise a patient's blood pressure pattern may be deemed as having a pattern of stable or astable, hypertensive or non-hypertensive, average-hypertensive or average-non-hypertensive, peak-hypertensive or peak-non-hypertensive, rapid-transition moderate transition, or slow transition, etc.

Computer system 120 comprises one or more processors operable to receive instructions and process them accordingly, and may be embodied as a single computing device or multiple computing devices communicatively coupled to each other. In an embodiment, processing actions performed by system 120 are distributed among multiple locations such as one or more local clients and one or more remote servers. In an embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

An embodiment of computer system 120 include computer software stack 125, which in some embodiments operates in the cloud, as a distributed system on a virtualization layer within computer system 120. An embodiment of software stack 125 includes a distributed adaptive agent operating system 129, which may be implemented as a platform in the cloud, and which is capable of hosting a number of services such as 122, 124, 126, and 128. An embodiment of services 122, 124, 126, and 128 run as a local or distributed stack in the cloud, on one or more personal computers or servers such as system 120, and/or a computing device running manager 140. In an embodiment, manager 140 operates in conjunction with software stack 125.

In an embodiment, variables mapping service 122 and records/documents ETL service 124 provide services that facilitate retrieving frequent item sets, extracting database records, and cleaning the values of variables in records. For example, variables mapping service 122 may perform functions for synonymic discovery, indexing or mapping variables in records, or mapping disparate health systems' ontologies, such as determining that a particular medication frequency of a first record system is the same as another record system. In an embodiment, these services may invoke software services 126. Software services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org); R-system modules or packages including tsDyn or similar services for facilitating implementation of nonlinear autoregressive time series models, tuneR for performing statistical operations, pracma for performing practical numerical mathematical functions, tseriesChaos for nonlinear time series operations, strucchange for testing, monitoring and dating structural change, psd for estimating the power spectral density, wavelets for computing wavelet transforms, seewave for estimating entropy, and arulesSequences or similar services for facilitating operations such as K-nearest neighbor distance calculations. Software packages 126 are associated with services 128, which include Apache Hadoop and Hbase framework, or similar frameworks operable for providing a distributed file system, and which in some embodiments facilitate provide access to cloud-based services such as those provided by Cerner Healthe Intent®.

Example operating environment 100 also includes storage 121 or data store 121, which in some embodiments includes patient data for a candidate patient and information for multiple patients; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data stores associated with the one or more EHR systems, such as 160, 162, 164, and 166 and patient manager 140. Further, although depicted as a single storage data store, data store 121 may comprise one or more data stores, or may be in the cloud.

Turning briefly to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in an embodiment, computer system 120 is a computing system made up of one or more computing devices. In an embodiment, computer system 120 includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

In an embodiment, computer system 120 is a multi-agent computer system with agents. A multi-agent system may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities and choices that communicate via declarative messaging and use abstractions to allow for future adaptations and flexibility. An agent has its own thread of control which promotes the concept of autonomy. Additional information about the capabilities and functionality of agents and distributed multi-agent operating systems, as they relate to these embodiments, is provided in U.S. patent application Ser. No. 13/250,072, filed on Sep. 30, 2011, which is herein incorporated by reference in its entirety.

Alternative treatment is analyzed for Blood Pressure.

In an exemplary embodiment, a comparison of circadian evaluations of alternative treatments is presented to a user for the condition of high blood pressure (hypertension). In this application, the comparison facilitates a user making a choice that normalizes autonomic control and blood pressure variability (BPV) and reduces spectral dispersion and polychromatic power spectral density, attenuating higher-frequency components. This assists in mitigating health risks associated with excessive BPV.

The renin-angiotensin-aldosterone system is strongly circadian and activates during nighttime sleep. Normally, there is a diurnal variation in blood pressure (BP), with a 10% to 20% decrease (15-20 mmHg for waking 180 mmHg) in systolic blood pressure (SBP) during sleep-a so-called normal "dipping" pattern. Abnormalities in the normal nocturnal dipping pattern of BP have been associated with worse cardiovascular outcomes, even in subjects who are normotensive. 24-hr ambulatory BP measurement remains the only technique to assess the "dipping" status of patients.

The coefficient of variation (CV % value) of SBP and the standard deviation (SD) value of both 24-hr SBP and daytime SBP have positive correlations with the onset of cardiovascular events. Increased blood pressure variability (BPV) is an independent risk factor for cardiovascular events and renal deterioration in hypertensive patients. For nearly any level of 24-hr mean BP, hypertensive patients in whom the BPV is low have a lower prevalence and severity of organ damage than patients in whom the 24-hr BPV is high.

Scheduling antihypertensive medications such as angiotensin II receptor blockers and angiotensin-converting enzyme inhibitors at bedtime or in the middle of the night, as opposed to awakening or breakfast time, increases the proportion of patients with properly controlled BP, enhances the sleep-time-relative BP decline towards a normal "dipping" pattern. Similarly, evening or bedtime administration of angiotensin-converting enzyme inhibitors (ACEIs) benazepril, captopril, enalapril, lisinopril, perindopril, quinapril, ramipril, spirapril, trandolapril, and zofenopril exerts more marked effect on the asleep than awake systolic (SBP) and diastolic (DBP) BP means. Likewise, the bedtime (in comparison with 'morning') ingestion schedule of angiotensin-II receptor blockers (ARBs losartan, irbesartan, olmesartan, telmisartan, and valsartan exerts greater therapeutic effect on sleeping BP, plus significant increase in the sleep-time-relative decrease in BP, with the additional benefit, which is independent of the drug's terminal half-life, of converting the 24-h BP profile into a more normal "dipping" pattern.

Because dipping status is determined by (a) sleep BP and (b) awake BP, it might be expected that the 2 determinants would have equal weight. However, it has been found that there are negligibly small differences among groups in the awake BP levels such that differences in dipping status were determined almost exclusively by differences in nocturnal BP level. Although there is evidence that an extreme dipping pattern may lead to nocturnal cerebral ischemia, there is also evidence that nondippers are at greater risk for cardiovascular morbidity than dippers, both for cardiovascular events and for progression of kidney disease. Thus, at the present time it is reasonable to suppose that a normal dipping pattern is optimal from a prognostic point of view, and hence that it would be appropriate to optimize antihypertensive therapy to lower nocturnal BP in nondippers but not in extreme dippers. This is exactly what we have observed with losartan. Administration such that peak plasma levels occur prior to midnight or prior to 06:00 can normalize extreme dippers, non-dippers, and risers and convert them to normal dippers.

Part of studying the application of medicine at different periods of time involves control of the medication delivery system. Several oral chronopharmaceutical delivery systems are available, including Diffucaps®, Egalet®, OROS®, Chronset™, GeoClock™, Codas™, and TIMERx™ technology. With regard to antihypertensive therapy, the Innopran XL™ formulation of the beta-blocker propranolol has been FDA approved. Additionally, the calcium-channel blocker verapamil has a dosage forms called Covera HS™ and Verelan PM™ that involve controlled-onset, extended-release delivery intended for administration at bedtime.

A typical hypertension management strategy is to maintain average SBP within a target range (usually below a target threshold high level). Other novel and therapeutic targets are advantageously be pursued. For example, minimization of blood pressure variability (BPV) as represented by measures such as SBP CV % are pursued. However, simple measures of BPV such as SBP SD or CV % have statistically low sensitivity for measuring antihypertensive effectiveness.

A non-invasive blood pressure monitor (NIBP) such as that illustrated in monitor 149 of FIG. 1C is designed to be wearable and affords higher-frequency data collection, of typically 100 samples per second. An NIBP monitor 149 processes signals from cardiac probe cluster 189 of one or more cardiac probes, and senses the related pulse pressure near the thumb in sensor 181. A variety of statistical metrics are available to be evaluated, at the higher frequency, including high rate pressure measurements by relating velocity of the pulse to pressure. However, high-frequency data may not in and of themselves yield improved sensitivity and specificity for therapeutic decision-making.

In an embodiment frequency-domain, time-frequency-domain or entropy spectral measures are used to identify a therapeutic target measure that achieves high sensitivity and specificity. These measures are useful for individual personalized treatment evaluation and comparison.

In the illustrative instance of managing a subject's blood pressure, the circadian, diurnal variation of the body's auto-regulation of blood pressure exhibits significant phase-variation on a daily basis. Blood pressure in a majority of subjects shows a daily cycling with higher blood pressure during the waking hours and lower blood pressure when asleep. For subjects with "conventional" schedules, increase in blood pressure roughly coincides with waking hours from approximately 07:00. In the evening, blood pressure decreases somewhat in advance of the time when the person retires in bed and remains low while recumbent or sleeping, a pattern referred to above as "dipping", and persons who exhibit this pattern are known as "dippers". Other characteristic patterns are also known, such as CHAT, non-dippers, hyper-dippers, and the like. These patterns, studied for more than 40 years, are associated with clinical disorders and elevated risk of adverse outcomes.

To mitigate such risk, a subject's open-loop, free-running, astable pattern of circadian blood pressure variation can be perturbed by changes in activity and by administration of vasoactive medications, such as antihypertensive drugs. By identifying the timing of antihypertensive treatment in a dose regimen and synchronized in a particular schedule that results in the lowest BPV metrics, an optimal chronopharmaceutical regimen for administration of medications can be devised that establishes a forced, multi-stable pattern. If ongoing monitoring and adjustment is done, then the optimization can be a closed-loop feedback regime.

It is an object to achieve a precisely timed dose relative to a circadian rhythm of one or more selected antihypertensives so as to respond in a best known way to the personalized biorhythms and circadian physiology of the individual. It is an object in one illustrative example to accomplish the personalization of an antihypertensive regimen to the individual circadian dynamics of each person.

Timing and/or dose-range of administration is iteratively adjusted within a treatment regime to evaluate alternative combinations or treatment regimens within a family, and thus to discover through longitudinal monitoring of the subject's BPV responses to the alternative treatment regimens or "forcing functions" embodied in the varied treatments. If the medication dose is too small, or if the pharmacokinetics of absorption-distribution-metabolism-excretion (ADME) of the drug(s) or formulation(s) in the subject is too slow, then negligible synchronization or entrainment of the circadian pattern will be achieved. If the dose is sufficiently large and the ADME pharmacokinetics are such as to present a relatively sharp concentration curve with a concentration nadir, then administration/dissolution/release, and steep ascent to a maximum concentration of plasma drug level Cmax reached soon thereafter, then several phenomena are observed:

(1) 1:1 synchronization or entrainment or phase-locking of the blood pressure variation to a new circadian cycle that is aligned with the administration/dissolution/release of drug;

(2) attenuation of diurnal phase noise or jitter of the circadian blood pressure cycling waveform;

(3) low-pass filtering of the circadian waveform spectrum, such that roll-off is approximately 6 dB per octave;

(4) augmentation of side-peak spectrum fine-structure at frequencies higher than the fundamental 11.6 µHz diurnal spectral peak;

(5) appearance of higher-order autoregressive structure;

(6) increase in cross-correlation between the meds administration (and corresponding plasma level drug concentration C(t)) forcing function and blood pressure;

(7) decrease in spectral entropy, symbol entropy, and other measures of longitudinal variability or chaotic fluctuation of blood pressure; and (8) decrease in the duty-cycle of the [higher] waking-phase blood pressure.

In an embodiment, an abnormal condition to be ameliorated or a sensitivity of the individual subject's response results in a recorded message being displayed to a patient, user, or clinician indicating termination or amendment of the current regime. For example, the detection of confirmed consumption of a medication coupled with increased variability of blood pressure, or a failure to lower average blood pressure results in a warning to terminate use of the current medication, or to switch to a contingency dosage (e.g. doubling the current dose of losartan from 50 mg to 100 mg). In an embodiment, an emergency contact phone number or web address is displayed to a user, suggesting contact between a clinician before continuing the current treatment regimen.

Noninvasive Ambulatory blood pressure monitoring (ABPM) has been progressing from research tool to clinical tool for stratifying risk and guiding therapeutic decisions. In the past clinical use focused on avoiding "white-coat" hypertension (associated with anxiety at being examined). It is now thought that there is a greater prognostic significance of ABPM in determining risk for target-organ damage. Clinicians involved in the care of patients with hypertension should familiarize themselves with the role of this technology and how to use it in an appropriate and cost-effective manner.

Pulsatile drug delivery systems capable of releasing a drug after a predetermined lag period in pulsed or controlled release manner are being developed for research. Depending on the effective therapeutic application of the drug, a variety of design strategies have been formulated in the pursuit of pulsatile release. Circadian (24-hr cycle) dependency of various physiological and pathological functions is well established, thus, it becomes imperative to develop a drug delivery system to achieve release of drug at specific site and time. Such systems are advantageous for drugs that have an extensive first-pass metabolism, exhibit biological tolerance, or need targeting of locally absorbed/active drug to a specific site in the intestine, and are useful for optimizing the therapy to chronopharmacological idiosyncratic processes of the individual.

Population studies show the direct benefit from self-measurement for guiding the treatment of patients with severe hypertension. Population studies separate groups of children with a positive vs. negative family history of high blood pressure, despite the difficulty of obtaining valid readings during the rest/sleep span, which are needed for a reliable estimation of the circadian parameters. Provided the results are chronobiologically analyzed and interpreted in the light of reference limits which are specific to self-measurement series as well as for gender, age and times of sampling, systematic self-measurement of blood pressure may yield a reliable assessment of the circadian variation for a majority of individuals. For those who have been validated in at least one 30-day/24-h profile, automatic ambulatory profiles are recommended as the main approach.

Over-swinging or CHAT (brief for Circadian Hyper-Amplitude-Tension), that is an excessive circadian variation in blood pressure (BP), has been associated with a large increase in cardiovascular disease risk, present even in the absence of an elevated BP itself. This usually asymptomatic condition is frequently overlooked by prior art methods that are based on spot-checks or intermittent measurements, because, for such patterns to be diagnosed, the measurements need to be taken around-the-clock, preferably for 7 or more days at the outset. Once diagnosed, however, a usual circadian BP pattern can be restored by means of certain pharmacologic interventions timed appropriately. Thereby, it is possible to reduce the risk of cardiovascular morbidity and mortality, cerebral ischemic events, and nephropathy in particular.

Non-invasive blood pressure (NIBP) time series acquisition entails periodic (generally every 3-5 min) measurements of Non-Invasive Blood Pressure (NIBP). Wearable continuous non-invasive vital signs devices are now available, e.g. Sotera Visi™, utilizing ECG-based wave-delay metrics to a plethysmographic sensor worn on the hand. Oscillometric measurement Fukuda Denshi Dynascope™ DS-7000 series, Dynatech CuffLink™, Critikon DynaMap™, Spacelabs, Welch-Allyn SpotCheck™ NIBP of wrist NIBP may overestimate SBP by approximately 10 mmHg compared to oscillometric arm band measurement unless the wrist is elevated to the level of the heart to eliminate hydrostatic offset bias.

Several difficulties for BP data evaluation have been encountered. Confounding of ascertainment of coupling of the pharmaceutical intervention's forcing function to the physiologic processes, by drift, autocorrelation, and spectral diffusion. Inadequate characterization of phase noise in the circadian variations, on account of excessive noise in the raw time series data. Failure to discover the detailed multi-scale dynamics of the physiologic processes and their response to the pharmaceutical intervention.

It is therefore valuable to establish a method for ameliorating such limitations and providing objective, quantitative means for determining the relatively best timing and/or dosage of medication so as to establish a phase-locking of the physiologic process to a therapeutically desirable circadian pattern, to sustain the phase-locking or entrainment in a manner that is consistent and stable with respect to passing time, and to impart a therapeutically desirable degree of variation to the time series. In certain cases, it is valuable to achieve a particular spectral profile exhibiting a desirable rate of attenuation (dB per octave) of high-frequency spectral content, or band-pass of specific frequencies, or a duty-cycle of a desirable targeted amount.

Some examples are beneficial for illustrating use of features of a system, method and computer-readable media for an embodiment. It is intended that a feature of one example may be employed in any other context or embodiment described herein. For example, a service that runs as an app on a mobile device could in another embodiment be performed as a local application in a tablet or desktop computer, or remotely on a server, or in a browser plug-in or web app.

Example 1: A blood pressure patient is currently medicated, but appears to be medicated at an insufficient level. For example, the patient has been taking 50 mg of Losartan at various ingestion times, but has experienced some severe headaches and nose bleeds in the afternoon particularly on stressful days.

Figure 10:
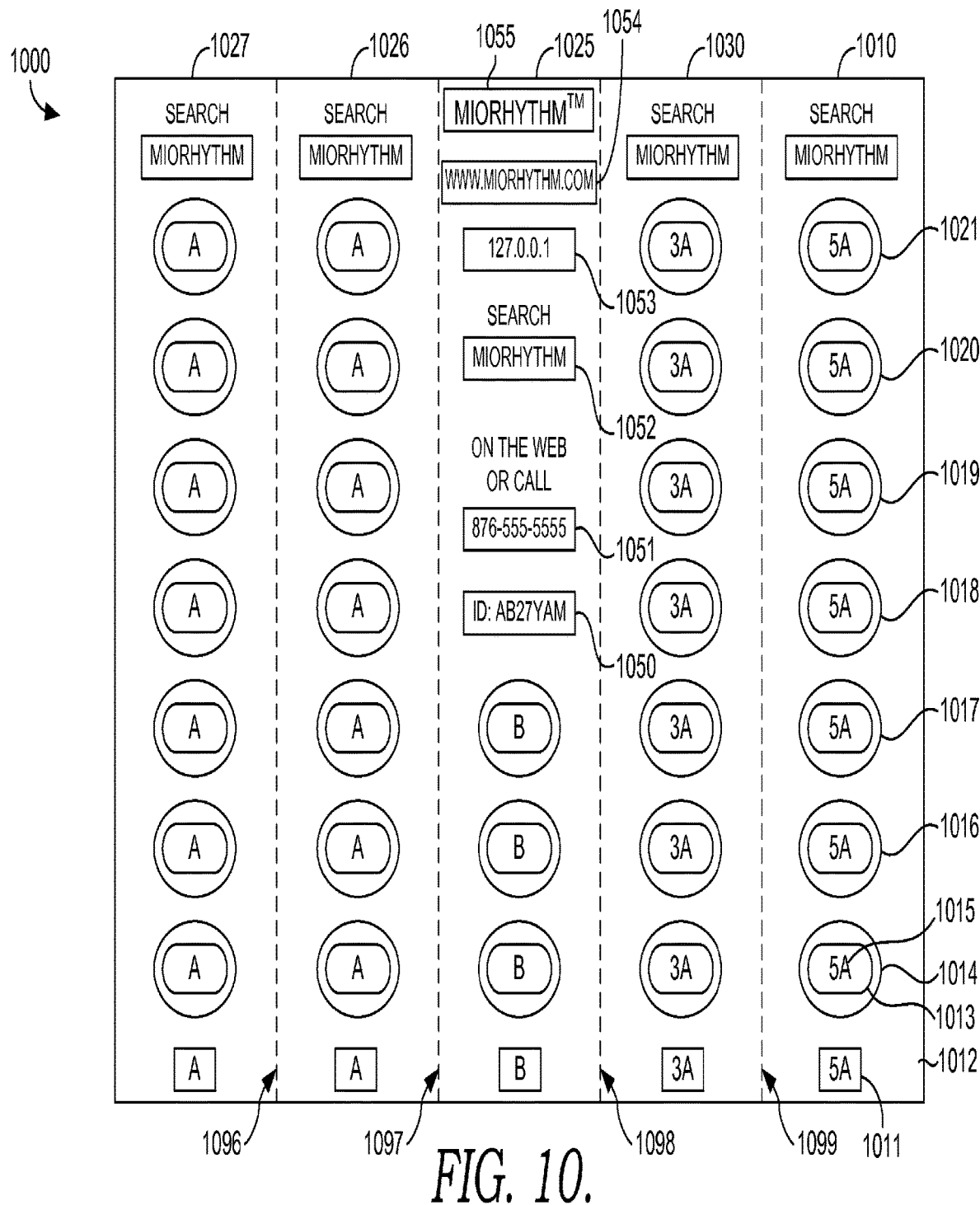
FIG. 10 illustratively depicts an article of manufacture that facilitates successfully following and logging at least a first treatment regimen.

A Clinician such as a prescribing physician gives a prescription for a Miorhythm™ evaluation pack 1000 as illustrated in FIG. 10, and loans the patient a monitor such as monitor 149 of FIG. 1C. In an embodiment, the evaluation package includes four different formulations labeled A, B, 3A, and 5A arranged in separable columns of constant medication 1027, 1028, 1025, 1030, and 1010, that may be separated by manually tearing package 1000 along perforated divisions 1096, 1097, 1098, and 1099. In an embodiment, dose pack 1000 is formed by selectively applying an adhesive to a foil backing layer to adhere the foil to transparent plastic front layer 1012 containing pills such as 1013 as shown in FIG. 10. In an embodiment, a label such as "5A" is provided on the dose itself such as label 1015 on pill 1013 as viewable in dose display container 1014, and/or on the packaging in label 1011 of constant formulation dosepack represented in column 1010. Advantageously, a patient tears along a perforation 1096 while taking dose A, and only need carry a single column such as 1027 while taking an "A" formulation dose. Similarly columns 1026, 1025, 1030 and 1010 are separable by perforations 1096, 1097, 1098 and 1099. An embodiment of a constant formulation dose pack has 32 cycles of dosage. An embodiment of a constant formulation dose pack has 10 cycles of dosage.

In an embodiment, the "A" formulation corresponds to a pulsatile application of 100 mg Losartan that applies medication nominally 20 minutes after ingestion, the "3A" formulation delays application of 100 mg of Losartan to 3 hours after ingestion. The "5A" formulation delays application of 100 mg of Losartan to 5 hours after ingestion. The "B" formulation is 5 mg amlodipine besylate that applies medication approximately 5 hours after ingestion. In an embodiment the dose sequence spectrum is chosen to center the medication application around a typical peak level. For example, with blood pressure medicine application, a peak plasma level between midnight and 6 a.m. would provide dosage delays centered about 3 a.m. for a patient who is thought to be a normal dipper. An embodiment puts at least one dosage application time in a period of normal peak, for example, between midnight and 6 a.m. for blood pressure application. In an embodiment, different dose levels are provided, such as a trial with 50 mg Losartan, or 150 mg Losartan for the same application time.

Figure 2:
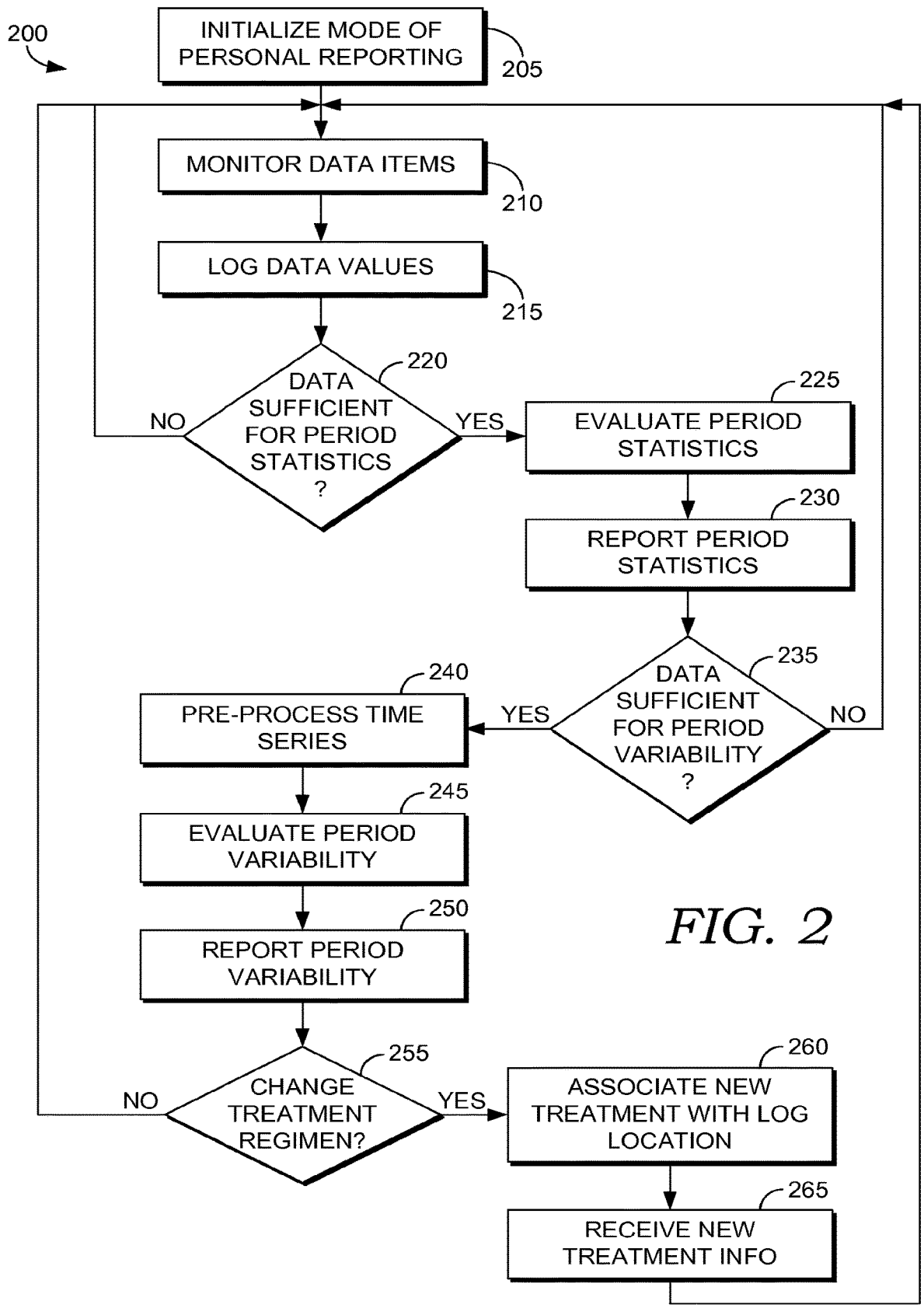
FIG. 2 depicts a flow diagram of a method of personal health evaluation, in accordance with embodiments of the present invention.

Turning now to FIG. 2, there is depicted in 100 a method for a computer to execute a method of personal health evaluation. At 205, a patient manager such as 140 is configured through a clinician evaluation template to present results to the patient on patient interface 141 after the clinician has released the information to the patient for viewing, explanation. In an embodiment a template includes a monitor identifier, a patient identifier, such as social security number and/or full name and zip code, and an identification code for the dose pack such as product ID code "AB27YAM" shown in identifier 1050. In an embodiment the template includes a set of patient instructions to guide patient through the use of the monitor device. In an embodiment, the patient is instructed to wear the monitor continuously with unmonitored stretches of no greater than a half an hour. In an embodiment, the template includes a planned number of therapies to test with associated prompts to the patient to remain on the treatment regimen, and to input patient compliance information indicating that the treatment regimen was carried out. In an embodiment, the template includes information such as gender (male or female), weight, height, body mass index, other conditions, other mediations, patient history, patient age, a diagnostic target, a clinical input to be monitored, a period statistic to be measured, a period variability measure to be evaluated, a variation, etc. In an embodiment a diagnostic target includes mean SBP below 135, entropy below 0.4, max SBP less than 160, a coefficient of variation less than 9%, a range of SBP less than 60, a significance less than 0.1, a spectral rolloff of at least 4 dB per decade. etc. In an embodiment a clinician selects a number of potential targets from a menu to be included in a template trial. In an embodiment, a clinician individually selects a level of a target for a patient based on the treatment context. In an embodiment, a user makes one or more such selections. In an embodiment a computer user indicates diagnostic targets by downloading a template or a message indicating targets to be analyzed.

In an embodiment at 205, a patient manipulates a patient interface 141 to acknowledge the beginning of a first treatment regimen. In an embodiment, a patient a LAN and/or enters a key or password for monitor 149 to automatically connect to a remote service and send data. In an embodiment, a patient enters an identifier from the dose pack 1000 such as identifier 1054, 1053, 1052, 1051 or 1050 to facilitate contact with a reporting service that evaluates period statistics and/or circadian statistics that provide individual performance of the patient for a treatment regimen based on logged data. For example, an identifier 1050 is associated with a description of all doses A, B, 3A, and 3B including all components and all levels of components relative to the evaluation pack. So that when a user inputs an indication that the patient is using formulation "A", the description is used to automatically indicate the type of medication or the active ingredients in the medication or the effective time of pulsatile delivery of the medication. In an embodiment, a patient enters a dose identifier such as "A" and a first time of actually taking the dose. The reporting service runs on interface 141 and/or computer 120 and/or interface 142 to report the individual performance based on logged data. In an embodiment, the same identifier such as "127.0.0.1", "876-555-5555" "miorhythm" or "ID: AB27YAM" appears on the dose pack 1000 in indicators 1050, 1051, 1052, 1053, 1054 or 1055 and also appears on a user interface such as 141 or 142 to confirm that the reporting service is performing the intended evaluation dose pack, and/or the intended dosing regimen. In this way, the user is confirmed that the contact with the selected reporting service is that intended by the physician and/or program and/or clinician performing the therapeutic evaluation of data logged for the patient. In an embodiment the index marking comprises one or more of a phone number, a URI, a web address, an IP address, a query string for a database search, a browser plugin name, a mobile phone application name and a computer application name. In an embodiment the index is used to contact a server that provides an application, personal web page, template, update, configuration data, dosage information, active ingredient information, component dosage information, or dosage sequence description related to the reporting service. In an embodiment a personal web page presents the plan description or the plan results.

In an embodiment a clinical template contains instructions to prompt the patient for a sequence of 5 different treatment regimens: first taking an "A" dose at 9 p.m. (21:00), then an "A" dose at 9 a.m., then a "5A" dose at bedtime (usually 10 p.m.), then a "3A" dose at bedtime, and then a "B" dose at bedtime. The template includes diagnostic target of determining a "normal dipper" pattern, an average SBP below 135, an entropy target of below 0.4, and a max SBP of 160. The template also includes an instruction to terminate the evaluation when all targets are met, and when the data is reviewed by a clinician and acknowledged by the patient.

In an embodiment at 205, a template within the monitor 149 is used to prompt the user with a treatment regimen, e.g. a display asks the patient "the first planned regimen is to take an 'A' dose at 9 p.m. (or 21:00); input a check at time medication 'A' is ingested". Patient uses touch surface of monitor 149 to put a checkmark on the surface of the monitor 149, and a time of ingestion is recorded. Alternatively, the patient could input a confirmation that therapy was performed within prescribed limits, or enter the digits indicating the time of ingestion, or the analysis software could assume regimen is carried out unless otherwise notified. In an embodiment, a patient records events and/or data that may be side-effects. In an embodiment, analysis software receives data that indicates side-effect such as a side-effect description, an indication of side-effect category, or an indication of time when the event was experienced. In an embodiment, suspected side-effects are presented to a user on a form, in decreasing frequency of occurrence, and the patient selects a GUI control adjacent to a listed item when the side-effect was experienced.

At 210, monitor 149 senses data items such as blood pressure value at a 100 Hz rate, and logs the data values at 215 into the internal storage of monitor 149. At 220 a test is performed to determine if there is sufficient data to calculate a first set of one or more period statistics. In this example, the period is approximately a day, and so an embodiment of a test at 220 determines whether or not approximately a day of data has been collected. Another embodiment additionally evaluates completeness of the data and/or the treatment regimen. If, for example, the regimen was followed closely enough, the monitor was not removed for too long of a time, the monitor sensing did not fail, the logging did not fail, for a sufficient period of time, the data is sufficient. If data is not yet sufficient, the method returns to 210 perhaps displaying current SBP and DBP and "insufficient data" for period statistics, but when sufficient data for a period statistic is available the method proceeds to 225 where period statistics are evaluated.

In an embodiment the mean SBP and the max SBP are calculated at 225 and at 230 are displayed on the monitor display screen of monitor 149. In an embodiment, at 230 all raw data is provided to a clinician who reviews performance data on clinician interface 142 at clinical system 164. In an embodiment, monitor 149 performs data reduction, assigning a calculated SBP and DBP to a longer time interval such as a 15 second interval, and the reduced data is transferred to clinical system 164 for review. In an embodiment, a pattern of daily variation such as "normal dipper" is determined by, for example, estimating the average SBP during a sleep period, and estimating the average SBP during a non-sleep period, and determining that the sleep SBP average is far enough below the waking SBP average (e.g. at least 10 mmHg). In an embodiment, an EEG monitor such as monitor 145 provides data to allow determination of a sleep or wake state for the determination of the sleep period and the non-sleep period. In an embodiment a user provides a user input indicating of a sleep time, and a wake time, and thereby indicates a sleep interval. For example, a 24 hour clock display is presented to the user, and a touch input indicates the approximate interval during which patient was asleep (e.g. an arc touch input on a circular clock face, or a line touch input on a linear day display). Alternatively the digits can be iteratively input or selected for sleep time and wake time by a user to indicate the sleep interval.

In an embodiment, a patient display on monitor 149 reports most recent data: (e.g. "current SBP=140 mmHg; current DBP=94 mmHg; Daily max SBP=170 mmHg, Daily average SBP=127 mmHg, current pattern 'normal dipper' with 50% confidence, current entropy=need more data")

In an embodiment a set of period statistics includes a mean, median, mode, standard deviation, variance, skewness, kurtosis, mean absolute difference, median absolute difference, a transition time, a rate of transition, a duration of a peak, a duration of a low, a rank order statistic, a coefficient of variation, etc. In an embodiment a statistic is formed over a cycle, a low partial cycle, a high partial cycle, high to low transition, a low to high transition, etc. In an embodiment a set of period statistics includes one or more of a minimum over a cycle, a maximum over a cycle, an average over a cycle, a range of variation, a duty cycle, an absolute deviation from a common reference, an absolute deviation of a delayed reference, a rank order statistic, a median, a standard deviation, a coefficient of variation, a variance, a transition time, a time of transition, a time between transitions, a time of variation and an interval of variation. In an embodiment a coefficient of variation is a ratio of an estimated standard deviation to an estimated mean.

At 235 a test determines if available data is sufficient to estimate period variability. In an embodiment a minimum number of real periods while following the treatment regimen is required to calculate variability statistics. For example, a minimum of days such as 4, 7, 8, or 32 is set in an embodiment. If there is insufficient data, in an embodiment, a variability display indicates "insufficient data", "need more data" or provides a cue, such as dashes "- - -", and the method returns to 210. In an embodiment a single cycle is virtually extended by down-sampling, and creating virtual repetitions of the day's data through circularly repeating data from a single day to create a number of virtual days. For example, if the monitor was not removed for more than one period of less than ½ hour, at least 120 samples from each hour of 15 consecutive seconds can be used to compute a 120 days of virtual data from a single day of blood pressure measurements. In an embodiment, missing data is interpolated to create one or more data items during the gap to create one or more cycles of data. In an embodiment, a patient confirms the continuation of the first treatment regimen by providing an indication that confirms the formulation and/or consumption time. In an embodiment, the patient provides an input indicating the time and type of therapy administered for the subsequent cycle.

When there is sufficient data, the method proceeds to 240 where the time series is pre-processed. In an embodiment, the time series is filtered to de-trend and/or demean a time series segment. In an embodiment, the time series is pre-whitened. In an embodiment, whitening involves treating a scalar segment as a vector and pre-multiplying an input vector by the square root of the eigenvalue matrix, and pre-multiplying the result by the eigenvector matrix.

In an embodiment pre-processing the time series includes removing an autoregressive, moving-average (ARMA) component by estimating the coefficients of the ARMA components, and removing them with a complementary ARMA filter.

In an embodiment, the pre-processing includes applying windowed processing to minimize a discontinuity at the boundary of the observation time. In an embodiment a two-phase window is applied to remove a first discontinuity at the daily boundary of a virtual day, and a second window is applied to remove a second discontinuity at the boundary of the complete observation time. In an embodiment multi-taper filtering is applied to the time-series.

At 245 period variability is evaluated. In an embodiment, to estimate a variability statistic the time series is converted to a transform domain, by computing a fourier transform, a wavelet transform, a walsh transform, or a discrete cosine transform. In an embodiment a fourier transform is followed by a frequency domain entropy calculation. In an embodiment a Shannon entropy is calculated. In an embodiment, symbol entropy is calculated. In an embodiment a Shannon Renyi spectral entropy is calculated. In an embodiment, entropy E, of a normalized spectrum Y having N values such that:

$$1 = \sum_{k=1}^{N} Y(k).$$

$$E = -\sum_{k=1}^{N} \frac{Y(k)\log(Y(k))}{\log(N)}.$$

In an embodiment, for a parameter $\alpha$, such that $0 \leq \alpha < 1$, $$E = \frac{1}{1-\alpha} \log_2 \left( \sum_{k=1}^{N} [Y(k)]^\alpha \right).$$

In an embodiment, to form a variability statistic an analysis is performed in the spectral domain to determine the rate of rolloff of Y(k). A rate of frequency domain attenuation is calculated. In an embodiment, a well-contained spectrum has approximately 6 dB per octave rolloff. In an embodiment, a well-contained spectrum has at least 4 dB per octave rolloff. In an embodiment the fraction of the spectral energy in a specific band is determined. For example, the rolloff over the first three octaves is determined. In an embodiment, a variability indication is determined to be low when at least a fraction (one third, one half, three quarters) of the energy is at or below the diurnal frequency (at or below the 11.6 micro-Hz fundamental). In an embodiment, a variability indication is determined to be low when the fraction of the energy in the first three octaves above the 11.6 micro-Hz fundamental is measured as a fraction of total energy is below a certain fraction (one half, one third, one eighth).

In an embodiment, a phase is calculated by estimating the values of $b_0$ and $b_1$ through standard nonlinear regression techniques in the two autonomous van der Pol equations:

$$\frac{dA(t)}{ac} \sim b_0 * A(t) - b_1 (A(t))^2 - \sin(\varphi);$$

$$\frac{d\varphi}{ac} \sim -b_3 * A(t)^{-1} * \cos(\varphi).$$

In an embodiment, the phase is used to estimate phase jitter as an indication of variability. In an embodiment time domain duty cycle, or coefficient of variation over a suitable time interval is used as an estimate that indicates of variability. In an embodiment phase is used to determine that the pattern is one of stable or astable.

In an embodiment, the shape of pattern variation is determined from the underlying time series. In an embodiment a classifier determines from data that the pattern is a normal dipping pattern, a reverse dipping pattern, a CHAT pattern, a non-dipper pattern, extreme dipper pattern, reverse dipper pattern, and riser pattern, etc. Likewise a patient's blood pressure pattern may be deemed as having a pattern of stable or astable, hypertensive or non-hypertensive, average-hypertensive or average-non-hypertensive, peak-hypertensive or peak-non-hypertensive, rapid-transition moderate transition, or slow transition.

In an embodiment evaluating period variability at 245 includes comparing a set of one or more period statistics for the current treatment regimen (second treatment regimen) to a first set of one or more period statistics from a first treatment regimen to provide a measure of relative performance. In the present example, where the second treatment regimen has been 100 mg LOSARTAN, administered at 21:00, the first treatment regimen may be, for example, an untreated treatment regimen that had been measured and archived at an earlier time, and so is available in the local or remote storage of the system. An embodiment of a comparison may then be a computer generated display that allows the performance of the untreated patient to be compared visually to the first treatment regimen such as the two corresponding curves presented in FIG. 7. Another example of a comparison is presented in the first and third columns from the left in FIG. 8, and the first, second and third columns from the left in FIG. 9. Another embodiment of a comparison is a qualitative comparison, such as a display informing a user of one or more relative metrics: "100 mg Losartan at 21:00 has only 5 of 7 desired targets met, achieved a normal dipping pattern, acceptable rolloff improvement, improved stability of rhythm, greatly improved entropy, unacceptable range, unacceptable max SBP, acceptable significance, acceptable entropy, acceptable CV".

An embodiment at 250 reports a measure or a comparison to a clinician on interface 142. An embodiment reports a measure or a comparison on patient interface 141. An embodiment reports individual performance by sending information containing individual performance during the second treatment regimen from monitor 149 to a remote computer such as 120. An embodiment reports individual performance as an indication of circadian stability category (very stable, stable, somewhat stable, astable, unstable). An embodiment of reporting gives a quantitative and/or visual expression of performance by listing entropy, phase jitter, phase category, phase variation, energy level, energy slope, significance, mean, max, min, range, SD, or CV. An embodiment of reporting indicates one or more of a fraction of usable data in an observation interval, an amount of redundancy in available data, and a current setting for test data sufficiency.

At 255 a decision is made whether or not to change the treatment regimen. In an embodiment, monitor 149 software determines based on clinician or user input whether or not the treatment regimen is the same as previous, and if it is, the method returns to 210 and continues monitoring and logging data for the treatment regimen into the same data record that is associated with the current treatment regimen for the current patient. In an embodiment, a patient continues with a predefined number of doses, for example, using all 7 doses in column 1027 of FIG. 10. In an embodiment, a warning is presented to a user instructing the user to move on to another treatment regimen in the planned sequence before exhausting the remedy in a column. For example, if the medication was apparently being applied out of phase with the patient's circadian rhythm, then the range, or average high value, or peak value may be similar to or even greater than the untreated values. One or more of such conditions can be flagged and/or used by the diagnostic program or by a clinician to move to a different and likely more advantageous stage of the therapeutic plan. In an embodiment, patient provides an input that indicates that the old treatment regimen continues, or alternatively an input that indicates the initiation of a new treatment regimen. A user thus elects a different treatment regimen, and informs the monitor 149 of current dose regimen and time by manipulating patient interface 141.

When a new treatment regimen is begun, at 260 the new treatment is associated with a log location. For example, as patient begins taking LOSARTAN at 9:00, a new log record is created. In an embodiment, a "wash-out" period intervenes between the 21:00 dose time of dose "A", and the first dose of "A" at 21:00. For example, the patient waits 36 hours after the last dose at 21:00 before taking the first dose at 9:00. In an embodiment, other washout periods of longer periods even as long as two weeks of no therapy are used. At 265 the computer receives new treatment information such as a formulation indication "A" and/or an ingestion time, e.g. 9:05 a.m. the method then returns to 210 to continue logging. In an embodiment, the planned sequence of treatments is carried out and all data is sent to a clinician for evaluation and for patient recommendation. In an embodiment, a first treatment regimen is logged in a first record, and a second treatment regimen is logged in a second record. In an embodiment the data for the first treatment regimen and the second treatment regimen are logged in the same record, and an indication is separately stored of the time that the second treatment regimen was begun. In an embodiment each record includes a patient identifier, a dose pack identifier, a monitor identifier, template information, stage of therapeutic treatment, etc.

Assuming for the present example, that the therapy treatment sequence proceeds as planned through the conclusion of third step, the patient completes consumption of column 1027 over 7 days at the planned time of 21:00. Subsequently, the patient completes consumption of column 1026 taking each dose at approximately 9:00. Finally, begins consumption of remedies in column 1010, taking pill 1013 in container 104 at 22:00, so that medication is applied at 3:00 through time delayed pulsatile delivery. The patient continues taking the pill in container 1016 on the second day, the pill in container 1017 on the third day, the pill in container 1018 on the fourth day, the pill in container 1019 on the fifth day, the pill in container 1020 on the sixth day, and the pill in container 1021 on the seventh day. As shown in the columns of FIG. 8 and FIG. 9 corresponding to an 03:00 dose time, in an exemplary target criteria all planned targets are satisfied with this dosing regimen.

Figure 4:
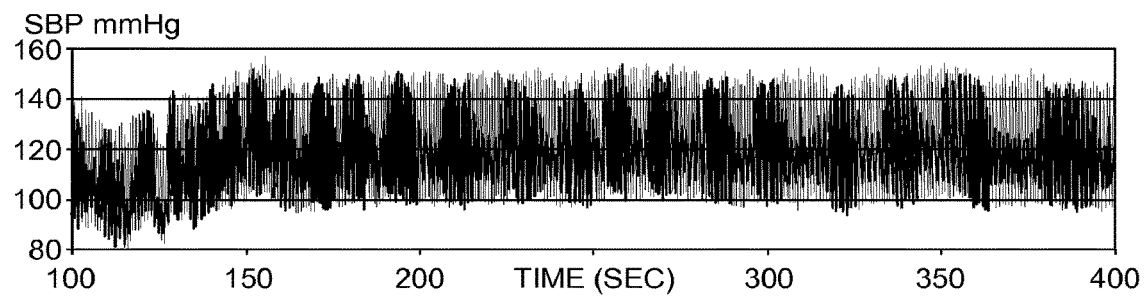
FIG. 4 presents a time series of non-invasive blood pressure (NIBP) sampled at 100 Hz, illustrating pressure in millimeters of Mercury for a patient.
Figure 5:
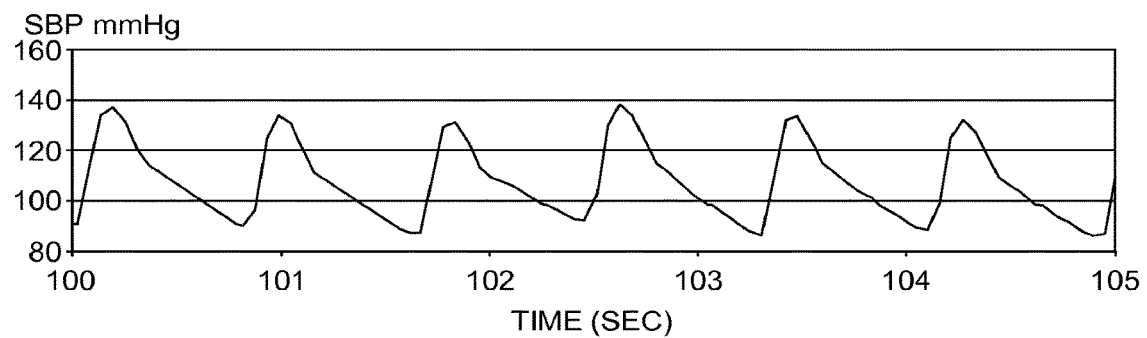
FIG. 5 presents an expanded view of a segment of a time series of NIBP sampled at 100 Hz, illustrating pressure in millimeters of Mercury for a patient.
Figure 6:
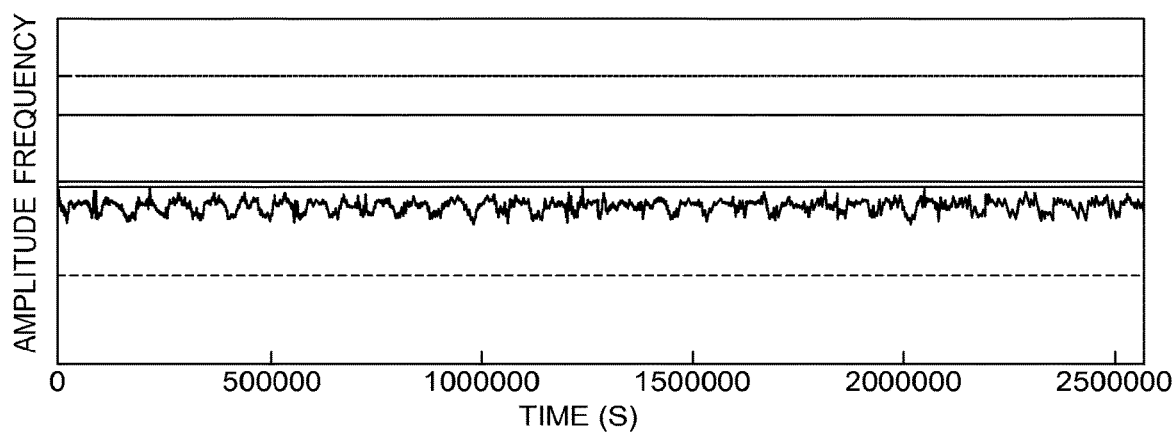
FIG. 6 presents an amplitude and frequency spectrum of an untreated hypertensive subject over a period of 32 days.

In an embodiment, a display is presented on user interface 141 indicating that "all therapeutic targets have been achieved for formulation '5A'," and that the corresponding formulation, delivering 100 mg of Losartan 5 hours after ingestion, to be taken at bedtime (10:00 p.m.), has been ordered from the patient's favorite pharmacy from the template record, and based on the trial pack outcome. In an embodiment, a clinician provides approval, and informs the user in a presentation form that the proper medication has been called into the pre-selected pharmacy. In an embodiment, the user acknowledges the accuracy of the trial by checking a box in the presentation form and/or also accepts any responsibility for inaccuracies in reporting or practicing a treatment regimen and/or agrees that impersonalized data may be used to be published or to aid future practice. In an embodiment, the completed form, and time of completion are sent to a clinical data store 121 and archived for future reference. In an embodiment, at least one of logged data values, period statistics, and individual performance are sent from a local computer such as monitor 149 to a remote computer such as 120. In an embodiment, a clinician evaluates the conclusion, and the total data at a computer such as 120 making use of clinician interface 142, and approves the automated selection prior to any results being sent to a patient. In an embodiment a clinician views a representative blood pressure time series as shown in FIG. 4 and/or detail of the representative blood pressure time series as shown in FIG. 5. In an embodiment a clinician views the overall trial amplitude and frequency characteristic as shown in FIG. 6. In an embodiment, raw data and/or raw blood pressure estimates are sent to clinician computer for processing at computer 120. In an embodiment, a clinical data store 121 aggregates all patient data from the trial. In an embodiment, patient data is recorded for study purposes under a sanitized personal identifier together with user identity non-specifying data for purposes of publication or additional annotation. In an embodiment, the clinical data store 121 is mined for similar demographic information so that past treatment results might be published and/or applied to future treatment plan development, practice, or advice.

Example 2: A Blood Pressure patient is borderline hypertensive and so reluctant to perform any treatment regimen at all, and therefore an evaluation pack 1000 is used that primarily supports lifestyle changes, nutritional supplementation, and an alternative medication therapy.

The following sequence of tests are planned: F (No lifestyle changes), G (Dietary changes, Exercise at bedtime), H (Dietary changes, Exercise at 5 a.m.), I (Dietary changes, exercise at noon), A (100 mg CoQ10 and 100 mcg vitamin K2 taken at bedtime and pulsed immediately), 3A (100 mg CoQ10 and 100 mcg vitamin K2 taken at bedtime and pulsed with a 3 hour delay), 5A (100 mg CoQ10 and 100 mcg vitamin K2 taken at bedtime and pulsed with 5 hour delay), and B (50 mg Losartan taken at bedtime and pulsed with 5 hour delay). Note that in this example, the first four trials involve creating a baseline record, and making only dietary changes (perhaps limiting sodium, low calorie diet, low meat diet, vegetarian diet, low inflammation diet, allergy/intolerance neutral elimination diet, etc.) The last four alternatives compare various nutritional supplements and pharmaceutical supplements, supported with the nomenclature that corresponds to dose pack 1000.

The patient is then loaned a monitor 149 without a template, but with an instruction sheet describing the different alternatives for the patient to explore for mitigating hypertension. At 205 the patient uses column 1025 from dose pack 1000 and uses an identifier to contact a Miorhythm server that downloads a PC application and/or a monitor 149 application to perform data analysis for a minimal nutritional supplement dose pack. The download includes a template describing active ingredients that correspond to A, B, 3A and 5A in the dose pack. In an embodiment the patient types in an identifier such as 1054 into a URL filed of a web browser or types identifier 1052 into a search box of a search service page presented in a web browser. The patient is then presented with a page allowing the patient to enter a dose-pack identifier such as that illustrated in identifier 1050. The patient is then presented with prompts allowing the patient to download desktop software and/or a monitor 149 application. The patient selects the appropriate download control and receives the software and template.

Upon running the personal evaluation application the patent selects variables to be monitored and locally estimated including 15 second blood pressure estimates, average SBP, peak SBP, and entropy. The patient enters a maximum bridging interval, that is an amount of time that the patient is allowed to remove the monitor and still use the data through down-sampling or interpolation. The patent sets the max bridging interval to be ½ hour. The patient sets a minimum trial duration of 7 days. The patient then selects a GUI control indicating that the first regimen to be followed is a baseline evaluation therapy which does not require any lifestyle changes, therapy or dosage. The patient types in an identifier F, and a description. The method proceeds to 210 where the corresponding blood pressure readings are sensed and recorded at 215, tests are continually performed at 220 until a sufficient amount of data is available. During the first few hours of use the patient's monitor displays only current SBP and DBP over the most recent valid 15 second interval, and at 220 loops back to 210.

After the first day of therapy F (no changes), at 220 the method proceeds to 225 where average SBP, and peak SBP are evaluated and displayed on monitor 149 at 230. The patient's circadian statistics are reported to the patient at 230 with an automated description of the risks present in the different categories. The monitor displays the first day of numerical results of tests, the patient "appears to indeed be borderline hypertensive of unknown circadian rhythm due to insufficient data." After seven days of monitoring, the method decides at 235 that data is sufficient for a circadian variability estimate. At 240 the time series is pre-processed by demeaning, whitening, ARMA filtering, detrending the time series. At 245 entropy is computed in the frequency domain and determined to be 0.3. The display of monitor 149 displays at 250 the baseline trial results that he is a circadian stable normal dipper with an average SBP of 137 mmHg, a peak SBP of 161 mmHg, and a baseline entropy of 0.3. The patient is skeptical of these results. In an embodiment the patient reviews the performance data and annotates the data record with explanatory notes for increased blood pressure. In an embodiment, the patient transfers the raw data from the monitor 149 over a wireless LAN to a personal computer that serves as a patient manager 140. The patient goes over his calendar from the week of trials and annotates with notes that correspond to high blood pressure readings. A note for Monday 10:00 a.m. is input indicating that the subject learned that he would have to substitute for his boss who was sick addressing 100 people who are hostile to his company. The following two hours are marked out in a timeline indicating the preparation and delivery of the speech. An annotation is added to Thursday of this week from 6 a.m. to 8 a.m. when the subject's car went off the road and was lodged in a snow-bank for two hours. An annotation is added for the time of exercise and duration of exercise. Other annotations are added, e.g. for exercise category (aerobic, non-aerobic, jazzercise, spinning, light weight-lifting, etc.)

Based on the subject's review of the events the subject determines that early morning exercise may be more advantageous, and so reduces the displayed statistic to be average SBP for all future trials, but to retain all statistics. At 255 the method receives activation of a GUI control that indicates patient would like to follow a new treatment regimen, and the method proceeds to 260 where a new log location is created for the new treatment regimen. The patient then uses monitor 149 to input a description and label for the second treatment regimen, which is denoted course H, and the method receives a description: "following a salt-restricted vegetarian diet and exercising at 5 a.m." In an embodiment an alarm is set by the monitor 149 to alert the user at each meal-time and at 6 a.m. prompting the user to confirm whether or not the lifestyle change was followed.

The patient then proceeds in a similar manner to complete trials G and I. The patient is then presented at 250 with a display on monitor 149 showing: (F average SBP=135 mmHg, G average SBP=135 mmHg, H average SBP=133 mmHg, I average SBP 140 mmHg). The patient then elects to follow treatment regimen A, 3A, and 5A and the method displays the results: (F average SBP=137 mmHg, G average SBP=135 mmHg, H average SBP=133 mmHg, I average SBP 140 mmHg, A average SBP 135, 3A average SBP 132, 5A average SBP 130). The patient then elects to try regimen B and receives the report that B average SBP is 115. The patient determines that he believes the prescription is the easiest thing for lowering risk, and so calls a clinician at a reporting service indicated in identifier 1051 on dose pack 1000. The clinician computer such as 120 makes a request for the patient's detailed trial information, and the patient confirms a request by manipulating a GUI control on interface 141. The clinician receives the summary results and detailed history, and calls in a prescription for the patient to the local pharmacy that he specifies for 50 mg Losartan which has a formulation to apply the medication 5 hours after ingestion, and with an instruction for the patient to take the mediation at about 10 p.m.

Example 3: An asthma patient has been troubled particularly by attacks following meals, and so a food allergy interaction such as milk is suspected.

The patient is given a prescription for an inhaler applicator that has an embedded device that records the time of application of medication, and loaned a blood pressure monitor 149. The patient is instructed to follow an allergen neutral "elimination" diet for three weeks and to begin wearing the blood pressure monitor at the beginning of the third week. The patient is then analyzed with two different periodic considerations. The first period is the circadian blood-pressure rhythm which is analyzed and considered as a nuisance parameter to be eliminated while we look for differential excursions that may be related to asthma and/or food reactions. The meal period is analyzed looking for an effect on blood pressure that might be associated with the times that an allergen is consumed. At the beginning of the fourth week, the patient begins following an allergen introduction regimen using food capsules arranged in columns as shown in dose pack 1000. For example, if a dairy allergy is suspected, label A could correspond to whole milk, 3A to lactose, 5A to milk protein, and B to whole soy. In an embodiment each column has four rows and a randomly selected subset of two capsules contain whole potato (or other neutral food) rather than the allergen being tested, so that the template associated with identifier 1050 records which dose has the allergen, but the patient is unaware of what is being consumed. In an embodiment a larger quantity of an allergen test-substance is consumed.

The patient uses one of the contact identifiers 1055, 1054, 1053, 1052, 1051 or 1050 to find a web-based analysis service. At 205, the patient enters personal identification information into the web-site and registers for a user-name and password. The patient enters a serial number such as identifier 1050 from the dose pack, and enters a serial number from the metered inhaler. One hour before mealtime the patient consumes the material as directed, and records personal symptoms at 210 into the web-form which are then logged at 215 to a personalized record. Advantageously, other information such as the Label "5A", the consumption time, and the consumption sequence of the pills counting from the label 1011 is entered by the patient. In an embodiment the dose label 1015 includes a consumption sequence number or letter. The inhaler monitors at 210 and records at 215 asthma application information as a function of time. The method returns from 220 to 210 until the patient completes the entire course of food introductions as directed. Every suspected allergen (such as milk, or milk protein) is tested in this way. The patient reports symptoms at 210 and the web server records at 215 symptoms such as nausea, bloating, head-ache, etc. In an embodiment, the patient manually enters asthma applications into the web form. In an embodiment, after the inhaler is returned to the pharmacist, or plugged into a USB port, the data that records inhaler applications is transferred to a computer 120 that aggregates data. The reduced blood pressure data is transferred from monitor 149 to computer 120.

At 220, it is determined that inhaler data, physical food reaction symptom information, and blood pressure information for the entire trial is present, and the method proceeds to 225. The method then computes the circadian statistics of blood-pressure and establishes a set of normal short term variability statistics relative to the circadian pattern of the individual. At 225 the meal period statistics are analyzed to determine meal period patterns such as elevated blood pressure, increased asthma attacks, or other noted symptoms. At 230 the period statistics are evaluated to indicate a significance relationship between asthma, blood pressure, and food allergen, and the results are presented to the user on a personalized web-form. At 235 the completeness of the data causes the method to proceed to 240 where the meal period, and the circadian variability series are pre-processed. At 245 the circadian and meal period variability are evaluated and at 250 the results are reported to the patient on the web form.

Figure 3:
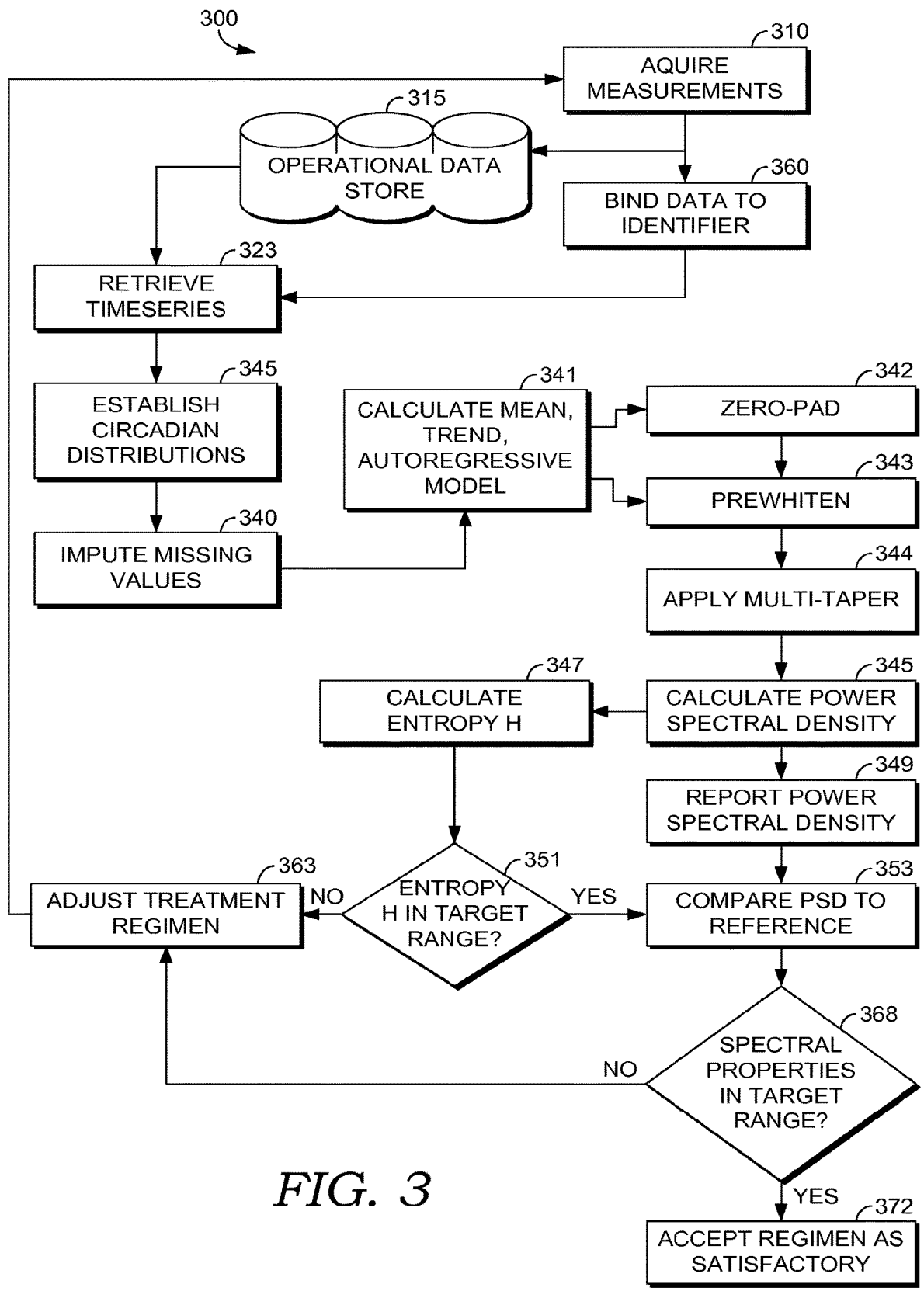
FIG. 3 depicts a flow diagram of an embodiment of personal health evaluation, in accordance with embodiments of the present invention.

Turning now to FIG. 3, there is shown in 300 a representative flow diagram of a method for personal health evaluation. Advantageously, an embodiment uses detrending, autoregressive moving-average (ARMA), and pre-whitening filtering of a digitized timeseries to remove the effects of drift, autocorrelation, and leakage or "bleeding" of adjacent spectral bands into each other. Multiple-tapering is performed in an embodiment of spectrum estimation. In an embodiment, samples are preferably be not less than 32 days in length in order to adequately represent the daily circadian variations under a reasonably diverse range of activities and exposures arising for the monitored subject over time. In an embodiment, Shannon and Renyi spectral entropy is calculated. In an embodiment symbol entropy is calculated. Entropy is used to assess the degree of disorder in a spectrum. In an embodiment robust nonparametric statistical methods are used, such as permutation tests, to assess the significance of differences between spectra (or lack thereof).

To illustrate the advantages of the present technology, a, a series of alternate schedules for administering a single, strong 100 mg oral dose of the rapidly-absorbed angiotensin receptor blocker, losartan, were explored (03:00; 09:00; 21:00; etc.). Subjects received informed consent according to applicable U.S. law and regulations. Baseline drug-holiday NIBP measurements were collected in each subject for a period of 32 days. Subjects who had other comorbid health conditions besides hypertension were excluded, as were subjects who required two or more antihypertensive medications for blood pressure control.

Under the experimental protocol, a two-week wash-out interval was interposed between a 32-day treatment period with one administration time and the next 32-day period. Subjects were randomized as to which administration time sequence. All of the losartan dosing schedules produced reduction in average blood pressure that would be regarded as nominally "effective" from a conventional perspective of hypertension management.

All of the 32-day timing regimens were monitored so as to establish administration timing compliance with a timing precision of +15 min.

It was not the aim to suppress BPV entirely but rather to discover the timing of administration that would result in diurnal phase-locking with the smallest phase jitter, the least power spectral density at frequencies higher than the diurnal 11.6 µHz fundamental, and the smallest entropy.

Records were randomly selected from a patient health records data warehouse, which is derived from Cerner electronic health record (EHR) from 100% of episodes of care that are incident upon the participating health institutions. The personally-identifiable information was removed in conformance with U.S. HIPAA law and regulations, and the de-identified data were stored in a separate, secure database. 32-day series of systolic blood pressure measurements (SBP) were acquired at least hourly intervals for patients treated for hypertension with monotherapy consisting of 100 mg per day of an angiotensin receptor blocker, losartan. For the derivation study, the subjects studied were required to have no other active health condition or diagnosis other than hypertension. The SBP data is cast into the form of a time series, and analyzed the sequences using the open-source R statistical packages psd, seewave, and tuneR.

Quasi-harmonic oscillations are seen in the SBP high sampling-rate time series and in SBP amplitude spectra from all sampling rates (FIGS. 4, 5 and 6). However, the noise in the spectra of baseline (untreated) was sufficiently large (low S/N ratio) that accurate ascertainment of phase and duty-cycle on any particular day was problematic. Therefore, determination of the phase-difference between baseline and the various treatment times is correspondingly imprecise. However the baseline measurements were used to estimate the phase using autonomous van der Pol equations, using standard nonlinear regression techniques. Strictly speaking, in the presence of high-intensity phase noise there is no synchronization of the astable circadian BP with the drug administration, and the phase difference φ does not oscillate linearly around some average value but instead intermittently jumps or "slips". Phase-slips were occasionally detected for the 21:00 administration time. Further study may be helpful to characterize this phenomenon.

Application in this instance was able to identify optimal timing for Losartan administration (03:00 for the subject shown in FIGS. 4 through 9). In such a case, where the optimal timing for Cmax(t) occurs during sleeping hours, a chronopharmaceutical formulation would be selected—one that produces release and absorption so as to produce the desired Cmax (t) peak at the optimal time. For example, if a formulation that produces Cmax 5 hours after administration were chosen, then that dosage form should be ingested at 22:00 (bedtime) to produce Cmax at 03:00 while the subject is asleep.

The foregoing and other objects, aspects and advantages may be understood from the following description of an embodiment with reference to FIG. 3 which presents in 300 a flow diagram that illustrates a system and method for generating a pre-whitened and multi-tapered power spectrum and enables computation of the symbol entropy of the spectrum. At 310, a time series of physiologic measurements is obtained for analysis. At 360 a monitoring device identity or an electronic medical record identity is bound to the individual patient identity and associated data. In an embodiment, acquired measurements and/or data reduced from raw measurements are stored in operational store 315. At 323 one or more time series of measurements are retrieved. In an embodiment, an archived time series recorded for the patient as a baseline characteristic is retrieved. In an embodiment, the time series is retrieved from a recording monitor.

At 345 the statistical distributions for daytime and nighttime time intervals are determined. At 340 time segments within the time series that have missing data are determined (e.g. due to sensor error, removed sensor, battery failure, etc.). In an embodiment, an appropriate distribution (night or day) for the location of the time interval is used to simulate data for the missing interval. In an embodiment, gaps are approximated in the mean by an interpolated linearly or non-linearly value between gap endpoints, with a randomizing variable added to simulate the sample to sample variation typically encountered approximately at the time of the gap.

At 341 one or more time-series characteristics are determined such as the mean, the trend, and the parameters of an Nth order autoregressive model. In an embodiment the method proceeds to 343 where the estimated characteristics are removed by pre-whitening filtering employing such techniques as de-meaning, detrending, and ARMA filtering as appropriate to the parameters estimated in 341. In an embodiment, at 342 the time series is zero-padded, and/or broken into multiple overlapping streams that are optionally phased with complementary windowing techniques to minimize edge artifacts. In an embodiment, Zero-padding or apodizing is used for the time series as needed, to prevent the artifacts caused by truncation or "end" effects in the frequency-domain spectra produced by Fourier or Wavelet transformation of the time series. At 344 multi-taper digital filtering is applied. At 345 the power spectral density (PSD) is calculated, and in an embodiment, proceeds to 347 where the entropy "H" is calculated. In an embodiment, at 347 the symbol entropy is calculated. In an embodiment, at 347 the spectral entropy of the spectrum is computed. In some instances, e.g. a sparsely-quantized time series, the symbol entropy may exhibit higher sensitivity than the Shannon-Renyi spectral entropy. In an embodiment at 351 the calculated entropy is compared to a target range, and if the entropy is outside of the target range, the method proceeds to 363 where an adjustment to the treatment regimen is made in an attempt to improve the individual patient performance as reflected in a time series and the method proceeds to 310 to acquire new measurements for the adjusted regimen.

In an embodiment from 345, the method also proceeds to 349 where the power spectral density is reported, e.g. by recording the power spectral density in a monitor 149 or in a computer 120. In an embodiment, the power spectral density is reported to a user on an interface 141 or interface 142 as depicted in exemplary fashion in FIG. 7. At 353 the power spectral density is compared to a reference. In an embodiment, a comparison is manifested in plotting two or more of the PSD curves as shown in the four exemplary curves of FIG. 7. In an embodiment, the PSD is analyzed and compared at 368 to a reference to provide a quantified analysis of the PSD. In an embodiment an amount of energy in the PSD in a defined band is compared to another PSD. In an embodiment, a fraction of energy in a portion of the band is compared to total energy. In an embodiment, the rolloff of the PSD in a defined band is computed and compared to a reference rolloff level such as 3, 4 or 6 dB per octave. At 368 if the spectral properties are not in the target range, then the method proceeds to 363 where an adjustment is made to the treatment regimen in an attempt to improve patient response. If the spectral properties are within the target ranges at 368 the method proceeds to 372 where the treatment regimen is accepted as satisfactory. In an embodiment two or more of entropy properties and spectral properties are compared to target values for the condition being treated. In an embodiment, a mathematical function combines two or more statistical properties and the result is evaluated and compared to one or more thresholds to determine whether or not to return to 363 for adjustment of the treatment regimen.

FIG. 4 shows non-invasive blood pressure (NIBP) time-series sampled at 100 Hz (Nyquist frequency 50 Hz), illustrating short time-scale fluctuations in peak systolic pressure on a beat-to-beat basis. FIG. 5 shows some detail from the same time series over a period of about five seconds. Sampling at less frequent intervals or averaging and storing only averaged values may fail to detect such fluctuations and, consequently, spectra derived by transforming such time series to frequency domain may not accurately display power spectral density at higher frequencies higher. FIG. 6 shows the amplitude frequency spectrum of an untreated hypertensive subject over a period of 32 days. The spectrum is monochromatic and stable as may be seen in the upper panel throughout. However, the diurnal dipping pattern results in small amplitude oscillations as may be seen in the lower panel around the 11.6 µHz fundamental.

Figure 7:
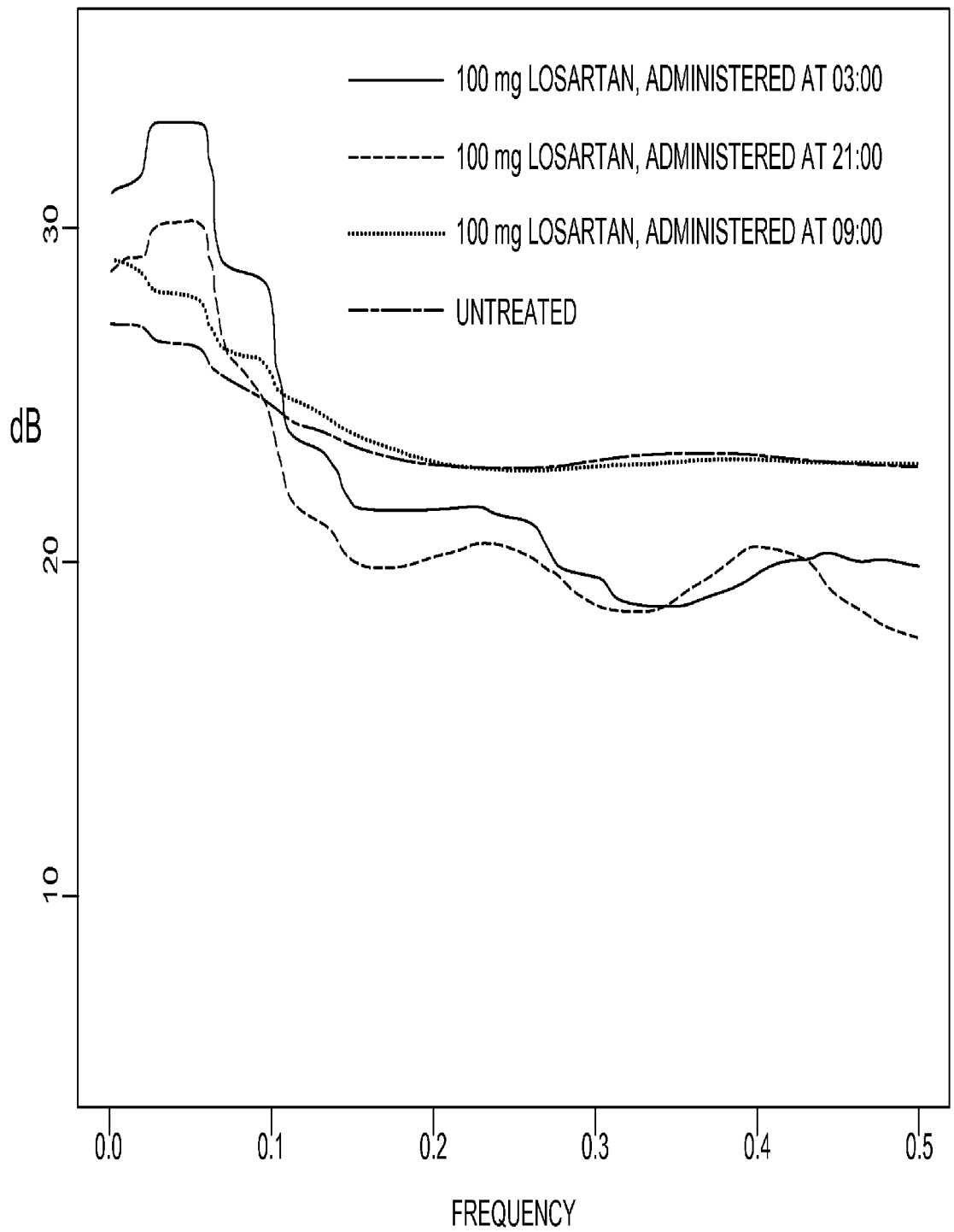
FIG. 7 presents power spectra for one subject filtered with a multiple-taper filter, for an untreated subject, and where the subject is treated with 100 mg losartan at three administration times.

FIG. 7 shows multiple-taper filtered power spectra for one subject, treated at 3 different administration times (100 mg losartan), plus the subject's spectrum in the baseline/untreated condition. FIG. 8 and FIG. 9 display entropy and other statistical measures for these time series and spectra.

Spectral leakage from the circadian BPV spectral peak into adjoining spectral bands can reduce the ability to detect significant chronopharmaceutics-induced changes, leading to false-negative conclusions of no difference. Spectral-leakage suppression may be used to strive for adequate sensitivity to detect spectral changes from chronopharmaceutical maneuvers. Thomson prolate tapers can accomplish this to some degree, while R-S and other multi-tapers do not exhibit the necessary leakage suppression effectiveness. As a result, in spectra that have large dynamic range, excessive power bleeds from the strong peaks into neighboring frequency bands of low amplitude-spectral leakage. Pre-whitening in some instances mitigates this problem, e.g. at least for "red" spectra. By nature, BPV spectra may have wide dynamic range as seen in FIGS. 4, 5 and 7, high-intensity low-frequency components and are "red" by virtue of being dominated by the circadian ½₄ hr-1 (11.6 µHz) low-frequency peak. Therefore, an embodiment performs pre-whitening on BPV time series samples. Power spectral density estimates can become badly biased (especially at lower frequencies) if a signal of the form $f(x)=Ax+B$ is not removed from the series. When we apply a de-trend function to the raw time series, a model of this form is removed over the entire series using a linear least-squares estimator.

Reduction to practice of an embodiment was accomplished using a computer running the Linux operating system, the open-source statistical software package R, and the R modules psd, tuneR, and seewave. However, a cloud-based computing configuration is an alternative embodiment. An additional embodiment makes use of a stand-alone tablet or smart phone or other mobile computing device equipped with suitable connectivity to the device(s) by which the time series are acquired.

When a power spectrum distribution for a process changes its shape, its mean (first moment) as well as other statistical moments may change as well. The power spectral density of a synchronized weakly nonlinear system with a small amount of noise may have one primary peak at the fundamental frequency of the forcing function. Increasing noise causes smearing of the peak and, may also result in the appearance of side-bands.

In an embodiment, the significance of changes between spectra sets in spectral intensity pairs, in light of signal variability within spectra sets, are determined, for example, using standard statistical techniques. A wide range of statistical techniques (both parametric and nonparametric) may be used to estimate the significance of difference in intensity pairs. Significance is expressed as a function of p-value. In an embodiment, a p-value represents the likelihood that an observed change between spectra sets in the distribution of intensities associated with a particular peak could have arisen by chance in the absence of differences between the samples. In an embodiment, ranks that come from statistical measures of the ability to correctly classify samples are used in combination with or in place of p-values.

In an embodiment, parametric methods are used to calculate p-values for differences between two or more spectra. A wide range of different parametric methods may be used. Examples of such methods include t-test and analogous tests not assuming Gaussian (or "normal") distributions of the data. In an embodiment where multiple conditions are present (more than two conditions) Analysis of Variance is used for each identifier. In an embodiment P-values are calculated using the minimum of a number of methods. For example, the analysis described above in which the means and variances of actual signals are used, and the analysis described above in which the means and variance of the implied distribution of logarithms of signals are used, thereby obtaining the union of all points of interest. In an embodiment, the resulting net p-value are multiplied by the number of methods used, by the Bonferroni method, or statistically corrected in some other way.

In an embodiment, a non-parametric method is used, for example, to produce a p-value in cases where the assumptions underlying a parametric method are not known to be appropriate. Many non-parametric tests would also accommodate more than two conditions. An example of a non-parametric method, involves replacing the difference between mean signal differences with its corresponding percentile in the observed (empirical) distribution.

In an embodiment, robust statistical methods are used to produce p-values. Robust statistical methods are methods that attempt to minimize the influence of extreme data points or other departures from distributional assumptions (thus in some contexts non-parametric tests, which do not depend on distributional assumptions, are considered robust). In an embodiment, Permutation tests are used. In an embodiment, P-value is assigned by rank within the list of observed values of the statistic. The statistical analyses can be performed on any function of the intensity pairs and/or identifiers and/or index(es).

In an embodiment, a system and method quantitatively identifies the optimum timing and dose-intensity of chronopharmaceutical treatment from one or a plurality of longitudinal time series of physiologic measurements, so as to best achieve target values of circadian variability in at least one physiologic measure. In an embodiment a time series is prepared by pre-whitening, by removing the mean, trend, and autoregressive model from the raw time series. In an embodiment the time series is prepared using Fourier or Wavelet transformation with multiple-taper filtering. In an embodiment the analysis of the frequency-domain spectra includes calculation of the power spectral density. In an embodiment, the analysis of the spectra includes calculation of the Shannon-Renyi spectral entropy or symbol entropy or other like entropy measures. In an embodiment a comparison of a sample spectrum is made to one or more reference spectra by robust nonparametric statistical tests. In an embodiment, the timeseries is sampled longitudinally with a precision and dynamic range of at least 6 binary digits (bits; 2.0% resolution) or, more preferably, up to about 12 bits (0.02% resolution). In an embodiment, the timeseries is sampled longitudinally for a time interval sufficient to encompass at least 2 octaves (f0·23 or 1 decade) of bandwidth in the frequency domain at the sampling rate utilized or, more preferably, up to about 16 octaves ($f_0 \cdot 2^{17}$ or 5 decades).

The exemplary embodiments discussed herein illustrated the invention by making use of a blood pressure sensor for blood pressure related conditions, and blood-pressure related therapies. Embodiments of the invention are intended to be used with other sensors, supplements, medications, therapies and conditions.

Although the invention has been described with reference to the embodiments illustrated in the attached drawing figures, it is noted that substitutions may be made and equivalents employed herein without departing from the scope of the invention as recited in the claims. For example, additional steps may be added and steps omitted without departing from the scope of the invention.

Many different arrangements of the various components depicted, as well as components not shown, are possible without departing from the spirit and scope of the present invention. Embodiments of the invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the invention.

It will be understood that certain features and subcombinations are of utility and may be employed without reference to other features and subcombinations and are contemplated within the scope of the claims. Not all steps listed in the various figures need be carried out in the specific order described.

The invention claimed is:
1. A system comprising:
a first monitor having a first systematic marking associated with a first dose of a first formulation remedy for a patient condition, the first systematic marking indicating a first treatment regimen associated with the patient condition;
a second monitor having a second systematic marking associated with a second dose of a second formulation remedy for the patient condition, wherein the second dose differs from said first dose, the second systematic marking indicating a second treatment regimen associated with the patient condition;
an index marking that facilitates contact with a reporting service; and
the reporting service that evaluates one or more circadian statistics of a patient associated with the patient condition based on logged data for a first time period associated with the first treatment regimen and a second time period associated with the second treatment regimen, the system generating a user interface that enables a first result metric depicting the one or more circadian statistics of the first treatment regimen to be compared visually to a second result metric depicting the one or more circadian statistics of the second treatment regimen and enables user input to select between the first treatment regimen or the second treatment regimen, wherein the first treatment regimen and the second treatment regimen have specified administration timings within a circadian cycle of the patient, wherein the user interface identifies a particular timing of the administration timings that is determined to entrain the circadian cycle of the patient to a target circadian pattern with an administration of a corresponding treatment regimen,
wherein the one or more circadian statistics correspond to physiological variables data of the patient.

2. The system of claim 1, wherein the first dose and the second dose differ in at least one of time of effective application of at least one component after ingestion, amount of a component ingredient in a corresponding formulation, number of components, and an active ingredient.

3. The system of claim 1, wherein the index marking comprises one or more of a phone number, a URI, a web address, an IP address, a query string for a database search, a browser plugin name, a mobile phone application name, and a computer application name.

4. The system of claim 1, further comprising:
a first unitary portable container displaying the first systematic marking; and
a third dose of the first formulation remedy, wherein said first dose and said third dose are packaged in the first unitary portable container.

5. The system of claim 4, further comprising:
a second unitary portable container displaying the second systematic marking; and
a fourth dose of the second formulation remedy, wherein said second dose and said fourth dose are packaged in the second unitary portable container.

6. The system of claim 5, wherein said first unitary portable container and said second unitary portable container are separably coupled to form a joint portable item.

7. A system comprising:
an index marking corresponding to a monitor, the index marking facilitating contact with a reporting service; and
the reporting service that evaluates one or more circadian statistics of a patient associated with a patient condition based on logged data for a first time period associated with a first treatment regimen and a second time period associated with a second treatment regimen, the system generating a user interface that enables a first result metric depicting the one or more circadian statistics of the first treatment regimen to be compared visually to a second result metric depicting the one or more circadian statistics of the second treatment regimen and enables user input to select between the first treatment regimen or the second treatment regimen, wherein the first treatment regimen and the second treatment regimen have specified administration timings within a circadian cycle of the patient, wherein the user interface identifies a particular timing of the administration timings that is determined to entrain the circadian cycle of the patient to a target circadian pattern with an administration of a corresponding treatment regimen,
wherein the one or more circadian statistics correspond to physiological variables data of the patient.

8. The system of claim 7, further comprising a first monitor having a first marking indicating the first treatment regimen associated with the patient condition.

9. The system of claim 8, wherein the first marking is associated with a first dose of a first formulation remedy for the patient condition.

10. The system of claim 9, further comprising a second monitor having a second marking indicating the second treatment regimen associated with the patient condition.

11. The system of claim 10, wherein the second marking is associated with a second dose of a second formulation remedy for the patient condition.

12. The system of claim 11, wherein the first dose and the second dose differ in at least one of time of effective application of at least one component after ingestion, amount of a component ingredient in a corresponding formulation, number of components, and an active ingredient.

13. The system of claim 7, wherein the index marking comprises one or more of a phone number, a URI, a web address, an IP address, a query string for a database search, a browser plugin name, a mobile phone application name, and a computer application name.

14. A system comprising:
a first unitary portable container displaying a first systematic marking
a second unitary portable container displaying a second systematic marking, wherein the first unitary portable container and the second unitary portable container are separably coupled to form a joint portable item;
an index marking associated with the joint portable item that facilitates contact with a reporting service; and
the reporting service that evaluates one or more circadian statistics of a patient associated with a patient condition based on logged data for a first time period associated with a first treatment regimen and a second time period associated with a second treatment regimen, the system generating a user interface that enables a first result metric depicting the one or more circadian statistics of the first treatment regimen to be compared visually to a second result metric depicting the one or more circadian statistics of the second treatment regimen and enables user input to select between the first treatment regimen or the second treatment regimen, wherein the first treatment regimen and the second treatment regimen have specified administration timings within a circadian cycle of the patient, wherein the user interface identifies a particular timing of the administration timings that is determined to entrain the circadian cycle of the patient to a target circadian pattern with an administration of a corresponding treatment regimen,
wherein the one or more circadian statistics correspond to physiological variables data of the patient.

15. The system of claim 14, wherein the first systematic marking is associated with a first dose of a first dose formulation remedy for a patient condition.

16. The system of claim 15, wherein the second systematic marking is associated with a second dose of a second dose formulation remedy for the patient condition, wherein the second dose formulation remedy differs from the first dose formulation remedy.

17. The system of claim 14, wherein patient treatment is adjusted based on a variability statistic indicating a measure of performance between the first treatment regimen and the second treatment regimen.

18. The system of claim 14, wherein the index marking comprises one or more of a phone number, a URI, a web address, an IP address, a query string for a database search, a browser plugin name, a mobile phone application name, and a computer application name.

\* \* \* \* \*